(12) United States Patent
Hoffman et al.

(10) Patent No.: US 8,003,129 B2
(45) Date of Patent: *Aug. 23, 2011

(54) ENHANCED TRANSPORT USING MEMBRANE DISRUPTIVE AGENTS

(75) Inventors: Allan S. Hoffman, Seattle, WA (US); Patrick Stayton, Seattle, WA (US); Oliver W. Press, Seattle, WA (US); Niren Murthy, Atlanta, GA (US); Chantal Lackey Reed, Del Mar, CA (US); Lawrence A. Crum, Bellevue, WA (US); Pierre D. Mourad, Seattle, WA (US); Tyrone M. Porter, Boston, MA (US); David Tirrell, Pasadena, CA (US)

(73) Assignees: University of Washington, Seattle, WA (US); Univeristy of Massachusetts, Boston, MA (US)

( * ) Notice: Subject to any disclaimer, the term of this patent is extended or adjusted under 35 U.S.C. 154(b) by 429 days.

This patent is subject to a terminal disclaimer.

(21) Appl. No.: 12/105,983

(22) Filed: Apr. 18, 2008

(65) Prior Publication Data

US 2008/0199957 A1      Aug. 21, 2008

Related U.S. Application Data

(63) Continuation of application No. 10/857,626, filed on May 28, 2004, now Pat. No. 7,374,778, which is a continuation of application No. 09/226,044, filed on Jan. 5, 1999, now Pat. No. 6,835,393.

(60) Provisional application No. 60/070,411, filed on Jan. 5, 1998.

(51) Int. Cl.
*A61K 9/14* (2006.01)
*A61K 9/16* (2006.01)
*A61K 47/00* (2006.01)
*A61K 9/127* (2006.01)

(52) U.S. Cl. ...... 424/501; 424/489; 424/450; 514/772.6

(58) Field of Classification Search .................. 424/450, 424/489, 501, 78.09; 514/772.6
See application file for complete search history.

(56) References Cited

U.S. PATENT DOCUMENTS 4,657,543 A    4/1987   Langer et al.
(Continued)

FOREIGN PATENT DOCUMENTS

WO       WO 93/14142 A1     7/1993
(Continued)

OTHER PUBLICATIONS

Abelev, G.I., "Alpha-Fetoprotein in Ontogenesis and Its Association With Malignant Tumors," *Advanced Cancer Research* 14:295-358, 1971.

(Continued)

*Primary Examiner* — Gollamudi Kishore
(74) *Attorney, Agent, or Firm* — Christensen O'Connor Johnson Kindness PLLC

(57) ABSTRACT

Compositions and methods for transport or release of therapeutic and diagnostic agents or metabolites or other analytes from cells, compartments within cells, or through cell layers or barriers are described. The compositions include a membrane barrier transport enhancing agent and are usually administered in combination with an enhancer and/or exposure to stimuli to effect disruption or altered permeability, transport or release. In a preferred embodiment, the compositions include compounds which disrupt endosomal membranes in response to the low pH in the endosomes but which are relatively inactive toward cell membranes, coupled directly or indirectly to a therapeutic or diagnostic agent. Other disruptive agents can also be used, responsive to stimuli and/or enhancers other than pH, such as light, electrical stimuli, electromagnetic stimuli, ultrasound, temperature, or combinations thereof. The compounds can be coupled by ionic, covalent or H bonds to an agent to be delivered or to a ligand which forms a complex with the agent to be delivered. Agents to be delivered can be therapeutic and/or diagnostic agents. Treatments which enhance delivery such as ultrasound, iontophoresis, and/or electrophoresis can also be used with the disrupting agents.

11 Claims, 8 Drawing Sheets

U.S. PATENT DOCUMENTS

| | | | |
|---|---|---|---|
| 5,362,308 | A | 11/1994 | Chien et al. |
| 5,451,411 | A | 9/1995 | Gombotz et al. |
| 5,501,584 | A | 3/1996 | Yamamoto et al. |
| 5,521,291 | A | 5/1996 | Curiel et al. |
| 5,547,932 | A | 8/1996 | Curiel et al. |
| 5,599,908 | A | 2/1997 | Raso |
| 5,603,931 | A | 2/1997 | Raso |
| 5,609,590 | A | 3/1997 | Herbig et al. |
| 5,656,609 | A | 8/1997 | Wu et al. |
| 5,753,263 | A | 5/1998 | Lishko et al. |
| 5,770,627 | A | 6/1998 | Inoue et al. |
| 5,807,306 | A | 9/1998 | Shapland et al. |
| 5,876,989 | A | 3/1999 | Berg et al. |
| 5,939,453 | A | 8/1999 | Heller et al. |
| 5,998,588 | A | 12/1999 | Hoffman et al. |
| 6,165,509 | A | 12/2000 | Hoffman et al. |
| 6,210,717 | B1 | 4/2001 | Choi et al. |
| 6,486,213 | B1 | 11/2002 | Chen et al. |

FOREIGN PATENT DOCUMENTS

| | | |
|---|---|---|
| WO | WO 96/40958 A1 | 12/1996 |
| WO | WO 97/04832 A1 | 2/1997 |
| WO | WO 97/09068 A2 | 3/1997 |
| WO | WO 98/33520 A1 | 8/1998 |
| WO | WO 99/33493 A1 | 7/1999 |
| WO | WO 99/39741 A2 | 8/1999 |

OTHER PUBLICATIONS

Anderson, D.C., et al., "Enhanced In Vitro Tumor Cell Retention and Internalization of Antibody Derivatized With Synthetic Peptides," *Bioconjugate Chemistry* 4(1):10-18, 1993.

Buschle, M., et al., "Receptor-Mediated Gene Transfer Into Human T Lymphocytes Via Binding of DNA/CD3 Antibody Particles to the CD3 T Cell Receptor Complex," *Human Gene Therapy* 6:753-761, Jun. 1995.

Cheung, C.Y., et al., "A pH-Sensitive Polymer That Enhances Cationic Lipid-Mediated Gene Transfer," *Bioconjugate Chemistry* 12(6):906-910, 2001.

Choi, Y.H., et al., "Lactose-Poly(Ethylene Glycol)-Grafted Poly-L-Lysine as Hepatome Cell-Targeted Gene Carrier," *Bioconjugate Chemistry* 9(6):708-718, 1998.

Cordes, E.H., and H.G. Bull, "Mechanism and Catalysis for Hydrolysis of Acetals, Ketals, and Ortho Esters," *Chemical Reviews* 74(5):581-603, Oct. 1974.

Ding, Z., et al., "Synthesis and Purification of Thermally Sensitive Oligomer-Enzyme Conjugates of Poly($N$-isopropylacrylamide)-Trypsin," *Bioconjugate Chemistry* 7(1):121-125, 1996.

Donbrow, M. (ed.), *Microcapsules and Nanoparticles in Medicine and Pharmacy*, CRC Press, Boca Raton, Fla., 1992.

Feijen J., et al., "Thermosensitive Polymers and Hydrogels Based on N-Isopropylacrylamide," *11th European Conference on Biomaterials*, Pisa, Italy, Sep. 10-14, 1994, pp. 256-260.

Fife, T.H., and L.K. Jao, "Substituent Effects in Acetal Hydrolysis," *Journal of Organic Chemistry* 30(5):1492-1495, May 1965.

Geisow, M.J., "Fluorescein Conjugates as Indicators of Subcellular pH. A Critical Evaluation," *Experimental Cell Research* 150:29-35, 1984.

Gold, P., and S.O. Freedman, "Specific Carcinoembryonic Antigens of the Human Digestive System," *Journal of Experimental Medicine* 122(3):467-481, Sep. 1965.

Guy, R.H., "Current Status and Future Prospects of Transdermal Drug Delivery," *Pharmaceutical Research* 13(12): 1765-1769, 1996.

Haensler J., and F.C. Szoka, Jr., "Polyamidoamine Cascade Polymers Mediate Efficient Transfection of Cells in Culture," *Bioconjugate Chemistry* 4(5):372-379, 1993.

Hansch, C., and W.R. Glave, "Structure-Activity Relationships in Membrane-Perturbing Agents," *Molecular Pharmacology* 7:337-354, 1971.

Hughes, J.A., et al., "Evaluation of Adjuvants That Enhance the Effectiveness of Antisense Oligodeoxynucleotides," *Pharmaceutical Research* 13(3):404-410, 1996.

Kircheis, R., et al., "Coupling of Cell-Binding Ligands to Polyethylenimine for Targeted Gene Delivery," *Gene Therapy* 4(5):409-418, 1997.

Kost, J., and R. Langer, "Responsive Polymer Systems for Controlled Delivery of Therapeutics," *Trends in Biotechnology* 10:127-131, Apr. 1992.

Kratz, F., et al., "Drug-Polymer Conjugates Containing Acid-Cleavable Bonds," *Critical Reviews in Therapeutic Drug Carrier Systems* 16(3):245-288, 1999.

Kyriakides, T.R., et al., "pH-Sensitive Polymers That Enhance Intracellular Drug Delivery In Vivo," *Journal of Controlled Release* 78:295-303, 2002.

Linhardt, J.G., and D.A. Tirrell, "pH-Induced Fusion and Lysis of Phosphatidylcholine Vesicles by the Hydrophobic Polyelectrolyte Poly(2-ethylacrylic Acid)," *Langmuir* 16(1):122-127, 2000.

Murthy, N., et al., "The Design and Synthesis of Polymers for Eukaryotic Membrane Disruption," *Journal of Controlled Release* 61:137-143, 1999.

Pawlak, M., et al., "Template-Assembled Melittin: Structural and Functional Characterization of a Designed, Synthetic Channel-Forming Protein," *Protein Science* 3:1788-1805, 1994.

Perales, J.C., et al. "An Evaluation of Receptor-Mediated Gene Transfer Using Synthetic DNA-Ligand Complexes," *European Journal of Biochemistry* 226(2):255-266, 1994.

Plank, C., et al., "The Influence of Endosome-Disruptive Peptides on Gene Transfer Using Synthetic Virus-Like Gene Transfer Systems," *Journal of Biological Chemistry* 269:12918-12924, Apr. 1994.

Prausnitz, M.R., et al., "Electroporation of Mammalian Skin: A Mechanism to Enhance Transdermal Drug Delivery," *Proceedings of the National Academy of Sciences of the USA* 90(22):10504-10508, Nov. 1993.

Prausnitz, M.R., "Reversible Skin Permeabilization for Transdermal Delivery of Macromolecules," *Critical Reviews in Therapeutic Drug Carrier Systems* 14(4):455-483, 1997.

Prausnitz, M.R., et al., "Transdermal Delivery of Heparin by Skin Electroporation," *Biotechnology* (N.Y.) 13(11): 1205-1209, Nov. 1995.

Press, O.W., et al., "Endocytosis and Degradation of Murine Anti-Human CD3 Monoclonal Antibodies by Normal and Malignant T-Lymphocytes," *Cancer Research* 48:2249-2257, Apr. 1988.

Ross, G., et al., "Gene Therapy in the United States: A Five-Year Status Report," *Human Gene Therapy* 7(14):1781-1790, Sep. 1996.

Schroeder, U.K.O., and D.A. Tirrell, "Structural Reorganization of Phosphatidylcholine Vesicle Membranes by Poly(2-ethylacrylic acid). Influence of the Molecular Weight of the Polymer," *Macromolecules* 22:765-769, 1989.

Thomas, J.L., et al., "Membrane Solubilization by a Hydrophobic Polyelectrolyte: Surface Activity and Membrane Binding," *Biophysical Journal* 67:1101-1106, Sep. 1994.

Thomas, J.L., and D.A. Tirrell, "Polyelectrolyte-Sensitized Phospholipid Vesicles," *Accounts of Chemical Research* 25:336-342, 1992.

Tolstikov, V.V., et al., "Influence of Endosome-Destabilizing Peptides on Efficacy of Anti-HIV Immunotoxins," *Bioconjugate Chemistry* 8(1):38-43, 1997.

Tycko, B., et al., "Rapid Acidification of Endocytic Vesicles Containing Asialoglycoprotein in Cells of a Human Hepatoma Line," *Journal of Cell Biology* 97:1762-1776, 1983 (abstract only).

Vinogradov, S.V., et al., "Self-Assembly of Polyamine-Poly(Ethylene Glycol) Copolymers With Phosphorothioate Oligonucleotides," *Bioconjugate Chemistry* 9(6):805-812, 1998.

Wang, L., et al., "Delivery of Antisense Oligonucleotides Using HPMA Polymer: Synthesis of A Thiol Polymer and Its Conjugation to Water-Soluble Molecules," *Bioconjugate Chemistry* 9(6):749-757, 1998.

Weaver, J.C., "Electroporation: A General Phenomenon for Manipulating Cells and Tissues," *Journal of Cell Biochemistry* 51:426-435, 1993.

Wilder, R.B., et al., "Radioimmunotherapy: Recent Results and Future Directions," *Journal of Clinical Oncology* 14:1383-1400, Apr. 1996.

Conformation of protein determines US/PEAA synergy

ENHANCED TRANSPORT USING MEMBRANE DISRUPTIVE AGENTS

The present invention is in the field of the delivery of therapeutic agents, and more particularly in the area of enhancement of transport or delivery of molecules into the cell cytosol, through cell barriers or layers of cells, or through lipid membranes, using membrane barrier transport enhancing agents alone or in combination with a stimulus and/or enhancer that modifies the structure and/or properties of the agents.

This application claims priority to U.S. Ser. No. 60/070,411 entitled "membrane Disruptive Agents" filed Jan. 5, 1998, by Allan S. Hoffman, Patrick Stayton, and Oliver Press.

STATEMENT REGARDING FEDERALLY FUNDED RESEARCH

The U.S. government has certain rights in this invention by virtue of an National Institutes of Health grant, National Institutes General Medical Sciences grant GM 53771-02.

BACKGROUND OF THE INVENTION

Specific, efficient delivery of therapeutic and diagnostic compounds to cells is a major goal of most pharmaceutical companies. A number of different approaches have been utilized to increase specificity and uptake. The most common has been to target the therapeutic or diagnostic agent to specific types of cells by conjugation of the agents to antibodies that recognize antigens specifically or predominantly associated with the cells. Other agents, such as polycationic complexes, liposomes, and lipid complexes, have been employed to increase uptake of compounds generally by cells.

There are several therapeutic agents which are only effective if they are delivered intracellularly, including genetic material and various proteins. Gene therapy requires the intracellular delivery of genetic material to treat genetic disorders, cause mutations in the genetic material in various cells, such as tumor cells, and bind to or interact with various sites in the cells to cause an effect. Examples of proteins include toxins which are only poisonous once they have been released from the endosome into the cytoplasm. To increase their specificity, immunotoxins have been prepared that include the toxin conjugated to an antibody that targets tumor-associated antigens. Immunotoxins have had limited success as therapeutics, however, in part due to the inadequacy of penetration into tumor nodules and ineffective delivery of the toxin into cytosolic ribosomes.

It is often difficult to deliver compounds, such as proteins, genetic material, and other drugs and diagnostic compounds, intracellularly because cell membranes resist the passage of these compounds. Various methods have been developed to administer agents intracellularly. For example, genetic material has been administered into cells in vivo, in vitro and ex vivo using viral vectors, DNA/lipid complexes and liposomes. DNA has also been delivered by synthetic cationic polymers and copolymers and natural cationic carriers such as chitosan. Sometimes the synthetic polymers are hydrophobically modified to enhance endocytosis. While viral vectors are efficient, questions remain regarding the safety of a live vector and the development of an immune response following repeated administration. Lipid complexes and liposomes appear less effective at transfecting DNA into the nucleus of the cell and may potentially be destroyed by macrophages in vivo.

Receptor mediated endocytosis offers an alternative means to target specific cell types and to deliver therapeutic agents intracellularly. Receptor-mediated endocytosis (RME) occurs when ligands bind to cell surface receptors on eukaryotic cell membranes, initiating or accompanying a cascade of nonequilibrium phenomena culminating in the cellular invagination of membrane complexes within clathrin-coated vesicles. Compounds which interact with specific cell surface receptors are employed to target specific cell surface receptors. The compounds are endocytosed into the endosomes once the compounds interact with the cell surface receptors. Linkages have been made directly with the compounds, or, in the case of DNA, through conjugation with polycationic polymers such as polylysine and DEAE-dextran which are then complexed with the DNA. Haensler et al., *Bioconj. Chem.*, 4:372-379 (1993).

Even after therapeutic agents are delivered intracellularly, normal trafficking in the cell can minimize their effectiveness. For example, certain antibody-antigen conjugates are readily endocytosed. However, after endocytosis, the antibody is not released into the cytosol but rather remains isolated in endosomes until it is trafficked to a lysosome for degradation. Press, O. W. et al., *Cancer Research*, 48: 2249-2257 (1988). Endosomes are membrane bound phospholipid vesicles which function in intracellular trafficking and degradation of internalized proteins. The internal pH of the endosomes is between 5.0 and 5.5. A toxin conjugated with this antibody will be similarly isolated in the endosome, and, if trafficked to a lysosome, will be rendered ineffective. Genetic material, being negatively charged, is often complexed with polycationic materials, such as chitosan and polylysine, for delivery to a cell. Both immunotherapy and gene therapy using polycation/nucleic acid complexes are limited by trafficking of the complexes by the cell from endosomes to lysosomes, where the antibody conjugates or nucleic acids are degraded and rendered ineffective.

Accordingly, a major limitation of many potentially useful therapies is that the agents, even if they can be targeted to the desired cells and endocytosed by the cells, often are not effectively released from endosomes into the cytosol, but are degraded by lysosomes.

Several methods have been proposed to avoid or minimize lysosomal degradation of these agents. One method involves including lysosomotrophic agents such as chloroquine in formulations used to administer therapeutic agents intracellularly. Another method involves disrupting the endosome so that the agent is delivered into the cytosol before it is transported to and degraded by the lysosomes. It is preferable to disrupt the endosome so that the material never comes in contact with the lysosomes. At least two pathways have been developed for disrupting the endosomal membrane. One method takes advantage of the pH inside the endosomes, and uses materials which are relatively hydrophilic at physiological pH (around 7.4) and relatively hydrophobic at the pH inside of the endosomes. Examples of such materials are carboxylic acid containing polymers such as the hydrophobic polyacid poly(2-ethylacrylic acid) (PEAA), which are negatively charged at alkaline pH and uncharged at the pH inside the endosome due to protonation of the carboxylic acid moieties.

PEAA has been shown to solubilize lipid membranes in a pH dependent manner, permeabilizing and solubilizing membranes at an acidic pH (approximately 6.3), while having no effect at alkaline pH. Thomas, J. L. et al., *Biophysical Journal* 67:1101-1106 (1994); Thomas, J. L. et al., *Acc. Chem. Res.*, 25: 336-342 (1992). It has been postulated that the effects of PEAA are due to its amphiphilicity rather than structure, consistent with a hydrophobically driven micellization process. A similar process has been hypothesized for the interaction of apolipoproteins, melittin, and other amphiphilic α-helix based polypeptides with lipid membranes.

Various peptides also disrupt endosomal membranes in a pH dependent manner. Examples of peptides shown to disrupt liposomes, erythrocytes, and endosomes, include viral peptides, such as influenza virus peptides and peptides that include the 23 amino terminal amino acid sequence of influenza virus hemagglutinin, and related peptides which viruses destabilize endosomal membranes in a pH dependent manner such as GALA (also known as EALA) which includes repeating glutamic acid-alanine-leucine-alanine blocks. These peptides have been conjugated with DNA complexes that utilized a receptor mediated endocytosis pathway for uptake into cultured cells. A strong correlation was observed between pH specific erythrocyte disruption and gene transfer. Plank, C. et al., *J. Biol. Chem.* 17(269):12918-12924 (1994); Hughes, J. A. et al., *Pharm Res.*, 13(3):404-(1996). Other peptides include melittin and derivatives, which are membrane channel formers. Pawlak, M. et al., *Protein Science* 3:1788-1805 (1994). GALA has been conjugated with a polycationic polymer (polyamidoamine cascade polymers, dendritic polymers synthesized from methyl acrylate and ethylenediamine), and the polycationic polymeric block has been complexed with plasmids encoding reporter genes. Haensler, J. et al., *Bioconj. Chem.*, 4:372-379 (1993).

None of these methods or materials have solved the transport or delivery problems. It would therefore be advantageous to provide improved compositions for delivering diagnostic and/or therapeutic agents to the cytoplasm of a cell without significant lysosomal degradation.

It is another object of the present invention to provide compositions for enhanced transport of diagnostic or therapeutic agents, including proteins and genetic material, or other molecules through other cell membranes, cell barriers or cell layers, or through lipid membranes.

It is a further object of the present invention to provide such compositions that can be controlled aid manipulated externally, for example, using non-invasive means such as ultrasound to enhance delivery or transport.

SUMMARY OF THE INVENTION

Compositions and methods for transport or release of therapeutic and diagnostic agents or metabolites or other analytes from cells, compartments within cells, through cell layers or cell barriers, or lipid membranes are described. The compositions include a membrane disruptive agent or "membrane barrier transport enhancing agent" and are usually administered in combination with an enhancer and/or exposure to stimuli to effect disruption, transport or release. In a preferred embodiment, the compositions include compounds which disrupt endosomal membranes in response to the low pH in the endosomes but which are relatively inactive toward cell membranes, coupled directly or indirectly to a therapeutic or diagnostic agent. Other disruptive stimuli can be used with the membrane barrier transport enhancing agent, such as light, electrical stimuli, electromagnetic stimuli, ultrasound, temperature, or combinations thereof. The compounds can be coupled by ionic, covalent, hydrophobic or H bonds to an agent to be delivered, to a ligand which forms a complex with the agent to be delivered, or to a carrier. Agents to be delivered can be therapeutic and/or diagnostic agents, including proteins or peptides, synthetic organic molecules, nucleotides or oligonucleotides, carbohydrates, metals, radiolabels, or combinations thereof.

In a preferred embodiment, the endosomal membrane disrupting compounds are polymers, most preferably pH sensitive polymers which are inert at physiological pH (around 7.4) but which disrupt the endosomal membrane at the pH range inside the endosome (between about 5.1 and 5.5). Suitable polymers include poly(alkyl)acrylic acids, cationic polymers, copolymers of the polymers with pH sensitive proteins and/or peptides which can disrupt endosomes at the pH range inside the endosomes, and copolymers with peptides which contain imidazole groups and/or other groups which are known to disrupt endosomal membranes. Optionally, the compositions can include compounds which minimize lysosomal function, enhance endocytosis or target the compositions to particular cell types.

Alternatively, or in addition, the composition can include ligands such as polycationic materials like polylysine or chitosan, which form a complex with the agent to be delivered, stabilizing the agent and in some cases further enhancing endocytosis by causing membrane disruption. The compositions can also include a carrier, for example, nanoparticles or microparticles, liposomes or lipid vesicles. The lipid vehicles, especially cationic liposomes, may themselves cause membrane disruption. The membrane disrupting agents can be incorporated onto, into or within these carriers. The compositions can be administered systemically or locally using known methodologies, in an amount effective to diagnose or treat a patient in need thereof. The materials are particularly useful for delivery of genetic material to cells in vitro, for example, for gene therapy. The compositions are also useful for manipulation of other types of cells such as bacterial cells, which can be readily exposed to an external stimuli to cause membrane disruption, including changes in pH.

Treatments which enhance delivery can also be used with the membrane disrupting agents. In a particularly preferred embodiment, ultrasound is used to enhance delivery or transport into or out of cells or through the skin. This is useful not only for drug delivery, but also transport of analytes such as glucose, which can then be measured and the amount present in the interstitial fluid correlated with blood levels. This treatment is also particularly useful for gene therapy into other cell types such as endothelial and smooth muscle cells, especially in the arterial environment, for example, for the treatment or prevention of restenosis. The treatment can be applied to the site before, at the time of, or following administration of the membrane disrupting agent. One advantage of ultrasound is that the membrane disrupting agent, preferably targeted to specific cells, can be administered systemically, allowing time for the agent to travel to a distal location, followed by administration of the ultrasound. The preferred type of ultrasound is high intensity focused ultrasound (HIFU). The ultrasound can be delivered by a variety of means, including the direct application of the transducer to the surface of the tissue to be treated, or at some distance removed from the tissue surface, in which both plane waves and focused acoustic waves can be utilized. Optimal frequencies typically range from a 20 kHz to 10 MHz, preferably less than 3 MHz.

DETAILED DESCRIPTION OF THE INVENTION

Figure 1A:
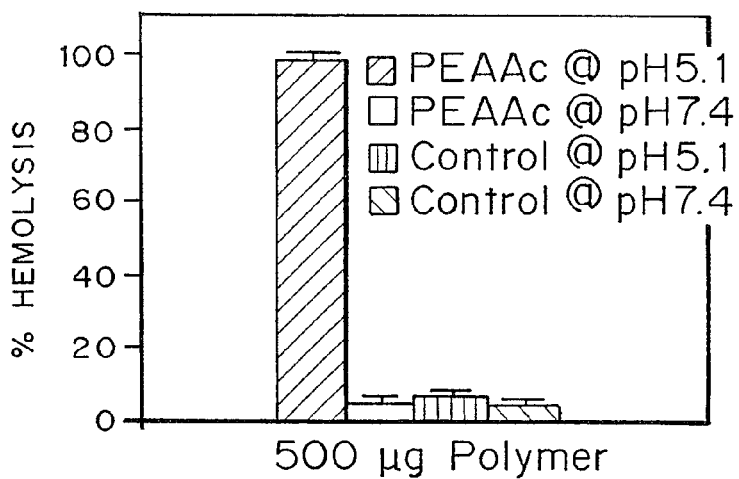
FIG. 1A is a graph showing the ability of poly(ethyl acrylic acid) (PEAA) to lyse erythrocytes as a function of pH. Percent hemolysis is shown at a solution pH of 5.1 and 7.4, for 500 µg PEAA and for control.

A. Compositions for Enhancing Membrane Transport and Methods of Manufacture Thereof I. Membrane Barrier Transport Enhancing Agents Any membrane disrupting agent can be used to alter transport through cell membranes, liposomes or other lipid vesicles, membranes within a cell or through a layer of cells such as the stratum corneum, which does not adversely affect the ability of the therapeutic or diagnostic agent to function following delivery, and which disrupts the membrane or interstitial spacing such that the agent to be delivered passes through the cell or cell layer(s). Although referred to herein as "membrane disruptive agents", the agents may not actually disrupt the membrane and therefore the term is used interchangeably with "membrane barrier transport enhancing agent". For example, a number of polymers respond with large physical changes to small changes in environmental conditions, such as solution pH, ionic strength, solvent composition, temperature, light, and electric field. These polymers are referred to as stimuli-responsive, environmentally sensitive, "intelligent" or "smart" polymers. Hoffman, A. S., "Intelligent Polymers in Medicine and Biotechnology", *Macromol. Symp.*, 98, 645-664 (1995); also in: *Artif. Organs*, 19, 458-467 (1995). In the case of endosomal membrane disrupting agents, it is preferred to use polymers that disrupt the membranes by virtue of the lower pH in the endosomes such that the agent to be delivered is delivered to the cytosol without significant degradation by the lysosomes.

Although described herein with reference to disruption of endosomal membranes as compared to cell membranes, cell barriers, layers of cells, or liposomal membranes, the agents can be used for delivery to cells, out of cells, or across cell layers or barriers such as the blood brain barrier, or liposomes or other lipid vesicles by disruption of membranes other than endosomal membranes, if the stimuli to induce disruption can be selectively provided at the cell membrane to be disrupted.

pH Sensitive Agents

Polymers

Examples of endosomal membrane disrupting agents include pH sensitive polymers which do not disrupt cell membranes at physiological pH but which disrupt the endosomal membrane at the pH range inside the endosomes, random, block or graft copolymers of these polymers with peptides which become hydrophobic at the pH range in the endosome and polymers, proteins and peptides which attack phospholipid bilayers.

Any polymer can be used which is not hydrophobic at physiological pH, typically in the range of between 6.8 and 7.5, and approximately 7.4 inside cells, but which becomes hydrophobic at the pH inside the endosomes (between 5.0 and 6.5). Polymers which include multiple carboxylic acid groups, for example, polymers with more than 0.5 carboxylic acid groups per monomer on average, tend to be relatively hydrophilic at pH ranges in which the carboxylic acid groups are deprotonated, and tend to be relatively hydrophobic at pH ranges in which the carboxylic acid groups are protonated. The pKa for carboxylic acid groups is such that they tend to be protonated at the pH range present in the endosomes.

Random, block and graft copolymers that include acrylate groups and alkyl substituted acrylate groups are preferred. Preferably, the alkyl group is a $C_{1-6}$ straight, branched or cyclic alkane. Preferred monomers for use in preparing the polymeric materials include poly(ethylacrylic acid) (PEAA), poly(propylacrylic acid) (PPAA) and poly(butylacrylic acid) (PBAA). Copolymers of these monomers by themselves or including acrylic acid can be used. An example of a random copolymer is EA-AA. This may be modified by grafting of either component to the backbone of the other component, or as a block copolymer of a block of one conjugated to a block of the other.

Random, block or graft copolymers of pH sensitive polymers with sulfonate groups can also be synthesized. The sulfonate groups will interact strongly via ion-ion interactions with the charges on the cationic polymer or lipid DNA carriers and should enhance the physical coupling of the sulfonated polymer with the cationic carrier. The carboxyl groups on the pH-sensitive polymers should not interact as strongly as the sulfonate groups with the cationic groups on the carriers. The pH sensitive polymers can be modified by inclusion of AMPS, a sulfonated propyl acrylamide monomer. In addition to pendant hydrophobic and —COOH groups in the polymers, monomers that have pendant sulfonate groups can be added (eg, using a monomer called AMPS, which is a sulfonated propyl methacrylamide monomer and is commercially available), which would permit strong ionic bonding of our membrane-disruptive polymer to a cationic DNA carrier, including cationic lipid micelles or liposomes, polymeric cations and dendrimers. The sulfonate —$SO_3$— group will couple much more strongly to a quaternary cationic group than will the —COO— group, and at the pHs of 5-6.5 within the endosome, only the —COOH group will be protonated, due to the low pK of the —$SO_3$— group.

The polymers can also include blocks of other polymeric materials, including polycationic blocks such as polylysine and chitosan that form complexes with genetic material. Such polycationic polymers are well known to those of skill in the art. The polymers can also be covalently coupled to one or more naturally-occurring polysaccharides, e.g. a hydrocarbon ester of carboxymethyl cellulose (CMC), hydrocarbon esters or amides of hyaluronic acid (HA). The hydrocarbons can be or can include cholesterol and other hydrophobic molecules.

Important variables of polymer composition which alter polymer characteristics include molecular weight ("mw") and its distribution, tacticity of the backbone polymer bond configurations, copolymer structure, degradable bonds, and polymer composition. For example, polymers can be synthesized in stereoregular forms (e.g., isotactic or syndiotactic forms, which are stereoregular), or atactic form, which lacks any stereoregularity. This can be controlled, for example, through selection of appropriate solvents during polymerization Copolymers are formed from two or more different monomers. These can be random copolymers, with random organization of the two monomers along the backbone of the polymer chain, or they may be block copolymers, with long segments of one polymer attached to relatively long segments of the other. They can also be graft copolymers, where one of the two components is coupled as a side chain to the other, which forms the copolymer backbone. The block or graft copolymers can contain segments that act to disrupt lipid membranes and other segments that can carry ionically or covalently coupled drugs, where DNA is an example of an ionically bound drug.

As demonstrated by the examples, random copolymers can be synthesized of conventional monomers to exemplify "molecular engineering" of the composition of copolymers to have membrane disruptive properties at pHs less than 7.4. Lowering the pH for these new copolymers will show sharp increases in hemolysis with decreasing pH that occur at different pHs for the different polymer compositions. Example 1 demonstrates that a 1:1 random copolymer of ethyl acrylate (EA) and acrylic acid (AA) can cause hemolysis of RBCs at low pH, as does the homopolymer of ethylacrylic acid (PEAA), which it mimics in composition. Example 1 also shows that random copolymers of EA-AA as well as random copolymers of propyl acrylate (PA) with AA, and butyl acrylate (BA) with AA, are effective hemolytic agents of different degrees at pH 5.5. If the hydrophobic comonomer content is increased sufficiently, the copolymers can cause hemolysis at higher pHs such as pH 7.4. The more hydrophobic polymer compositions that are membrane disruptive at pHs above 6.0, eg, up to 7.4, may be most suitable for enhancing transdermal or transmucosal permeation in the presence of physical stimuli such as ultrasonic, electric or electromagnetic fields.

Peptides

Peptides which lose their charge at a lower pH and become hydrophobic, thereby altering their structure or other properties, disrupting the endosomal membrane in the process, can be used as polymeric blocks with the pH sensitive polymers described above. Examples of such peptides include viral and bacterial peptides, such as influenza virus peptides, peptides that include the 23 amino terminal amino acid sequence of influenza virus hemagglutinin, and peptides that mimic the manner in which viruses destabilize endosomal membranes in an acidification dependent manner. Such peptides mimic the structure of virus proteins which destabilize endosomal membranes. For example, peptides based upon the influenza virus protein hemagglutinin (HA) have been shown to undergo a structural change at lower pH due to protonation of carboxyl groups, triggering formation of an α-helical conformation. These amphipathic helices can then penetrate and cause disruption of the endosomal membrane. Examples of suitable peptides include EALA (also known as GALA), a peptide having a repeating glutamic acid-alanine-leucine-alanine structure, and mellitin.

These peptides can be incorporated into polymers, for example, the pH sensitive polymers described above. GALA-polyacrylic acid graft copolymers can be prepared, for example, by polymerizing an N-acryloxysuccinimide monomer via free radical polymerization, reacting the resulting poly-(N-hydroxysuccinimide) (poly-NHS) with a desired mole ratio of GALA in a polar aprotic solvent such as dimethylsulfoxide (DMSO), and hydrolyzing the remaining unreacted NHS groups to yield the graft co-polymer. The mole ratio of GALA to the acryloxy monomers should be less than one, such that carboxylic acid groups are present in the final polymer. Without the remaining carboxylic acid groups, the ability of the polymer to respond to changes in pH is limited. The incorporation of peptides into these polymers dramatically enhances and in some cases can confer activity on the peptides when they are otherwise ineffective.

Structurally related graft co-polymers can be prepared by substituting different NHS-substituted monomers, for example, methyl acryloxy succinimide, ethyl acryloxy succinimide, propyl acryloxy succinimide, butyl acryloxy succinimide, and combinations thereof.

Block copolymers can be prepared by synthesizing sequences of EALA attached to sequences of mellitin. Block copolymers can also be prepared that include different synthetic polymers using group transfer polymerization techniques. Conjugates of two different polymers or peptides may be more effective than either one alone, or physical mixtures of the two. Purification of the conjugate from the free components can be performed using ion exchange chromatography, for example, strong cation exchange. It is advantageous to remove the free polymer from the conjugate of the polymer and the agent to be delivered. The free polymer, being negatively charged, can be separated from the conjugate via ion exchange chromatography. The negative charge serves to alter the affinity of the antibody for the cation exchange matrix, making it possible to separate free antibody from the conjugate as well.

Phospholipid Bilayer Disrupting Agents

Polypeptides and polymers which include imidazole groups can also be endosomal membrane disrupting agents which function by attacking the phospholipid bilayer at a lower pH. The imidazole groups hydrolyze phosphate esters and carboxyl esters. Hydrolysis of lipids leads to the formation of lysophospholipids and fatty acids, both of which destabilize phospholipid bilayers and cause the disruption of cell membranes. Accordingly, these polymers and peptides can be used as polymeric blocks and coupled to the pH sensitive polymers and proteins described above.

Suitable polymers and polypeptides include polymers including vinyl imidazole monomeric units and proteins and peptides containing histidine residues. For example, monomeric ethyl acrylic acid can be copolymerized with vinyl imidazole. At pH 7.4, this polymer will not interact with the lipid bilayer; however, at low pH this polymer will become hydrophobic and interact with the endosomal membrane, bringing the imidazole group close to the phospholipids, where it can hydrolyse them and cause membrane disruption. Polyimidazole has its greatest catalytic activity when it is half protonated and half deprotonated. The pKa of polyimidazole is about 6.5, and hence should have greater activity in endosomes. These polymers and polypeptides can be used to form block or graft copolymers with the pH sensitive polymers and peptides described above.

Agents Sensitive to Other Stimuli

Agents can also be used which are sensitive to other stimuli including temperature, light, electrical stimuli, radiation, and combinations thereof, alone or in further combination with pH sensitive agents. Illustrative polymers described herein are temperature-, pH-, ion- and/or light-sensitive polymers. Hoffman, A. S., *Artif. Organs*, 19, 458-467 (1995); Chen, G. H. and A. S. Hoffman, "*Macromol. Chem. Phys.*, 196, 1251-1259 (1995); Irie, M. and D. Kungwatchakun, *Maokromol. Chem., Rapid Commun.*, 5, 829-832 (1985); and Irie, M., *ACS Polym. Preprints*, 27(2), 342-343 (1986).

Temperature Sensitive Polymers

Temperature sensitive polymers are described by Feijen, et al., 11*th European Conf. on Biomtls.*, 256-260 (1994); Monji and Hoffman, *Appl. Biochem. and Biotech.*, 14, 107-120 (1987); Monji, et al., *Biochem. and Biophys. Res. Comm.*, 172, 652-660 (1990); Park, et al., *J. Biomtls. Sci. Polymer Ed.*, 4, 493-504 (1993); Chen and Hoffman, *Bioconj. Chem.*, 4, 509-514 (1993); Ding, et al., *Bioconj. Chem.* 7, 121-125 (1995); Chen and Hoffman, *Macromol. Chem. Phys.*, 196, 1251-1259 (1995); Takei, et al., *Bioconj. Chem.* 4, 42-46 (1993); Takei, et al., *Bioconj. Chem.*, 4, 341-346 (1993); (18) Takei, et al., *Bioconj. Chem.*, 5, 577-582 (1994); Matsukata, et al., *J. Biochem.*, 116, 682-686 (1994); Chilkoti, *Bioconj. Chem.*, 5, 504-507 (1994).

Illustrative embodiments of the many different types of temperature-responsive polymers are polymers and copolymers of N-isopropyl acrylamide (NIPAAm). PolyNIPAAm is a thermally sensitive polymer that precipitates out of water at 32° C., which is its lower critical solution temperature (LCST), or cloud point (Heskins and Guillet, *J. Macromol. Sci.-Chem*. A2: 1441-1455 (1968)). When polyNPAAm is copolymerized with more hydrophilic comonomers such as acrylamide, the LCST is raised. The opposite occurs when it is copolymerized with more hydrophobic comonomers, such as N-t-butyl acrylamide. Copolymers of NIPAAm with more hydrophilic monomers, such as AAm, have a higher LCST, and a broader temperature range of precipitation, while copolymers with more hydrophobic monomers, such as N-t-butyl acrylamide, have a lower LCST and usually are more likely to retain the sharp transition characteristic of PNIPAAm (Taylor and Cerankowski, *J. Polymer Sci.* 13: 2551-2570 (1975); Priest et al., *ACS Symposium Series* 350: 255-264 (1987); and Heskins and Guillet, *J. Macromol. Sci.-Chem*. A2: 1441-1455 (1968). Copolymers can be produced having higher or lower LCSTs and a broader temperature range of precipitation.

Temperature-responsive polymers such as poly(NIPAAm) have been conjugated randomly to affinity molecules, such as monoclonal antibodies, for example, as described in U.S. Pat. No. 4,780,409; and Monji and Hoffman, *Appl. Biochem. Biotechnol.* 14: 107-120 (1987). Activated PNIPAAm has also been conjugated to protein A, various enzymes, biotin, phospholipids, RGD peptide sequences, and other interactive molecules.

By randomly copolymerizing a thermally-sensitive NIPAAm with a small amount (e.g. less than 10 mole percent) of a pH-sensitive comonomer such as AAc, a copolymer will display both temperature and pH sensitivity. Its LCST will be almost unaffected, sometimes even lowered a few degrees, at pHs where the comonomer is not ionized, but it will be dramatically raised if the pH-sensitive groups are ionized. When the pH-sensitive monomer is present in a higher content, the LCST response of the temperature sensitive component may be "eliminated" (e.g., no phase separation seen up to and above 100° C.). Graft and block copolymers of pH and temperature sensitive monomers can be synthesized which retain both pH and temperature transitions independently. Chen, G. H., and A. S. Hoffman, *Nature,* 373, 49-52 (1995).

Polymers Sensitive to Other Environmental Stimuli

Polymers sensitive to other environmental stimuli such as ion concentration, ion affinity and differential solubility are reported by Fujimura, et al. *Biotech. Bioeng.,* 29, 747-752 (1987); Nguyen and Luong, *Biotech. Bioeng.,* 34, 1186-1190 (1989); Taniguchi, et al., *Biotech. Bioeng.,* 34, 1092-1097 (1989); Monji, et al., *J. Biomtls. Sci. Polymer Ed.,* 5, 407-420 (1994); Chen and Hoffman, *Biomtls.,* 11, 631-634 (1990); Stayton, et al., *Nature,* 378, 472-474 (1995).

Polysaccharides such as carrageenan change their conformation, for example, from a random to an ordered conformation, as a function of exposure to specific ions such as K+ or Ca++. A solution of sodium alginate may be gelled by exposure to Ca++. Other specific ion-sensitive polymers include polymers with pendant ion chelating groups, such as histidine or EDTA, etc. A lipid or phospholipid group can also be chemically or ionically coupled to the membrane-disruptive polymer backbones, to facilitate its insertion into cationic lipid micelle or liposome DNA carrier systems. This could be done, for example, by conjugating a fatty alcohol to the —COOH pendant group to form an ester group, or by conjugating a dipalmitoyl phosphatidyl ethanolamine to the —COOH pendant group to form an amide group. Lipid groups could also be chemically-coupled to a terminal group of the polymers. If the sulfonated monomer AMPS described above is used in the membrane disruptive polymer, then one could ionically-complex a cationic lipid to the polymer to facilitate its insertion into cationic lipid drug carrier systems.

Light-Sensitive Polymers

Light-responsive polymers usually contain chromophoric groups pendant to or along the main chain of the polymer and, when exposed to an appropriate wavelength of light, can be isomerized from the trans to the cis form, which is dipolar and more hydrophilic and can cause reversible polymer conformational changes. Other light sensitive compounds can also be converted by light stimulation from a relatively non-polar hydrophobic, non-ionized state to a hydrophilic, ionic state. It is also possible to incorporate multiple environmental sensitivities in the same polymer, such as temperature and light sensitivity, by copolymerization.

In the case of pendant light-sensitive group polymers, the light-sensitive dye, such as aromatic azo compounds or stilbene derivatives, may be conjugated to a reactive monomer (an exception is a dye such as chlorophyllin, which already has a vinyl group) and then homopolymerized or copolymerized with other conventional monomers, or copolymerized with temperature-sensitive or pH-sensitive monomers using the chain transfer polymerization as described above. The light sensitive group may also be conjugated to one end of a different (eg temperature-) responsive polymer. A number of protocols for such dye-conjugated monomer syntheses are known.

Light-sensitive compounds may be dye molecules that isomerize or become ionized when they absorb certain wavelengths of light, converting them from hydrophobic to hydrophilic conformations, or they may be other dye molecules which give off heat when they absorb certain wavelengths of light. In the former case, the isomerization alone can cause chain expansion or collapse, while in the latter case the polymer will precipitate only if it is also temperature-sensitive.

Light-responsive polymers usually contain chromophoric groups pendant to the main chain of the polymer. Typical chromophoric groups that have been used are the aromatic diazo dyes (Ciardelli, *Biopolymers* 23: 1423-1437 (1984); Kungwatchakun and Irie, *Makromol. Chem. Rapid Commun.* 9: 243-246 (1988); Lohmann and Petrak, *CRC Crit. Rev. Therap. Drug Carrier Systems* 5: 263 (1989); Mamada et al., *Macromolecules* 23: 1517 (1990). When this type of dye is exposed to 350-410 nm UV light, the trans form of the aromatic diazo dye, which is more hydrophobic, is isomerized to the cis form, which is dipolar and more hydrophilic, and this can cause polymer conformational changes, causing a turbid polymer solution to clear, depending on the degree of dye-conjugation to the backbone and the water solubility of the main unit of the backbone. Exposure to about 750 nm visible light will reverse the phenomenon. Conversion of the pendant group from a hydrophilic to a hydrophobic state can also cause individual chains to expand or collapse their conformations. Such light-sensitive dyes may also be incorporated along the main chain of the backbone, such that the conformational changes due to light-induced isomerization of the dye will cause polymer chain conformational changes. When the polymer main chain contains light sensitive groups (e.g. azo benzene dye) the light-stimulated state may actually contract and become more hydrophilic upon light-induced isomerization.

Light can be used as a stimulus, for example, which converts a cationic dye to a neutral, more hydrophobic dye, thereby releasing anionic DNA and also producing a more hydrophobic molecule which can disrupt endosomal membranes.

Treatments to Enhance Membrane Disruption

As described above, membrane disruptive agents are delivered to the cells or cell barrier where transport is desired, at which point a stimuli, such as a change in pH at the site, or external stimuli such as light or temperature change, is applied and the membrane is disrupted. Disruption can also occur due to the combined effects of the membrane disruptive agent with the physical treatment which enhances the efficacy of the treatment, such as application of ultrasound, an electrical field, a electromagnetic field, iontophoresis, electroporation or a combination thereof.

Ultrasound

Ultrasound will typically be applied using devices which are commercially available. These devices have a therapeutic range of between about 20 kHz and 10 MHz, and are preferably used for topical application at less than 3 MHz. In one embodiment in which it is desirable to induce cavitation, a low intensity ultrasonic (US) field (one that will produce cavitation) is applied to cells in suspension in the presence of the membrane-disruptive polymers. As demonstrated by the examples, the polymers significantly enhance cell membrane disruption and release of molecules over that induced by the ultrasound alone. The effective dosage of membrane disrupting agent can be determined empirically, measuring cavitation (acoustically or by production of free radicals or chemical tracers such as iodine) or by measuring transport or release of material from within the cells or by endocytosis and intracellular trafficking of drugs in cells. Since the skin is slightly acidic, it should be possible to molecularly engineer the polymer composition to specifically promote transdermal permeation of drugs in the presence of a cavitating ultrasound field.

The ultrasound can be applied continuously or pulsed. The ultrasound can be applied to cells in suspension, or directly to cells in tissue or transdermally, using an appropriate ultrasound medium, before, during or after administration of the membrane disruptive agents.

Electrical Fields

Iontophoresis, electroporation, or other applications of electrical fields, to enhance transport are well known technologies. These can also be used in combination with administration of the membrane disruptive agents to enhance membrane disruption. Electrical fields may be applied as low voltage, continuous electrical fields, or high voltage, pulsed electrical fields. The electric field can be applied to induce an electrophoretic fow of charged molecules across the skin or cells (iontophoresis). Electroporation is the use of an electrical field to disrupt a cell layer or membrane.

Radiation

Types of radiation including ionizing radiation and photodynamic therapy may also be useful in combination with the membrane disruptive agents, especially those which are light responsive. In photodynamic therapy, light of the correct power and wavelength is absorbed by photosensitizers when then utilize the absorbed energy to convert oxygen which is normally in the triplet state to singlet oxygen, which is a potent cell killer. The latter is particularly effective in transport of cytotherapeutic drugs into tumor cells.

II. Diagnostic and Therapeutic Agents

Any therapeutic agent, prophylactic agent or diagnostic agent can be ionically or covalently linked, directly or indirectly, to an endosomal membrane disrupting agent, so long as the linkage does not interfere with the activity of the therapeutic or diagnostic agent following administration to the cell and endocytosis. The agent can be directly coupled to the endosomal membrane disrupting agent or indirectly coupled, via another compound coupled to the endosomal membrane disrupting agent, such as an endocytosis enhancing agent, a targeting compound, a compound decreasing lysosome function, or to a ligand attached to an endosomal membrane disrupting agent which binds to the therapeutic or diagnostic agent, such as a polycationic polymer which binds nucleic acid.

The therapeutic and diagnostic agents can be nucleosides, nucleotides or oligonucleotides, proteins or peptides, polysaccharides and other sugars, synthetic inorganic and organic compounds, metals or radioactive compounds or molecules.

Nucleosides, nucleotides, and oligonucleotides include oligomers or polymers of naturally occurring or modified nucleotides, including naturally occurring or modified purine and pyrimidine bases, 2' and 3' modifications such as O-alkyl, halo and azide modifications, and modifications of the phosphate linkages, for example, substitution of phosphorothioate linkages for phosphate linkages. Oligonucleotides include RNA and single and double stranded DNA nucleic acid sequences. The molecules can be antisense molecules which bind to complementary DNA to inhibit transcription, genes, aptamers, triplex helix-forming compounds, ribozymes and external guide sequences for ribozymes, DNAzymes, DNA plasmids, and viral vectors. Many plasmids and viral vectors are commercially available and a number have been used in clinical trials, especially adenoviral vectors, retroviral vectors, and adeno-associated viral vectors. Vectors will usually incorporate the gene to be delivered in phase and under the control of appropriate regulatory agents for expression in the cell where the material is to be delivered. Genes may be marker genes, genes encoding defective or missing proteins, or genes encoding a lethal protein.

Preferred compounds for killing cells include glycoprotein-based toxins such as ricin, the B chain of the diphtheria toxin, and peptides derived from adenovirus, influenza virus, and the GALA peptide. A representative toxin is ricin. Ricin is a naturally occurring glycoprotein heterodimer that includes an A-chain with N-glycosidase activity capable of inactivating 60S eukaryotic ribosome subunits, and a B-chain capable of binding to cell surface molecules (e.g., galactose residues for ricin B). The A-chain must be delivered to the cytosolic ribosomes for the cells to be killed. Since these toxins bind to virtually every cell via the B-chain, they lack the specificity required to be effective chemotherapeutic agents. Other toxins ribosylate and thereby inactivate elongation factor 2 which is required for protein synthesis. Other representative toxins are abrin, modeccin, *Pseudomonas* exotoxin, bryodin, mistletoe lectin, Shiga toxin, *Escherichia coli* labile toxin, Pertussis toxin, cholera toxin, anthrax toxin, viscumin, saporin, gelonin, momordin, trichosanthin, and pokeweed antiviral protein. Toxins can be conjugated to an antibody specific for targeted cells. Polysaccharides such as heparin can also be used, where the polysaccharide binds to receptors on the cell surface. Compounds with a wide range of molecular weight, for example, between 100 and 500,000 Daltons can be used.

When the agent to be delivered is a toxin, and the endocytosis enhancing agent is an antibody targeted to the cells to be killed, the resulting conjugate is an immunotoxin which can be effectively delivered to the cytosol. The carbohydrate moiety present in the Fc regions of antibodies is a convenient location for conjugation. When oxidized, these carbohydrate regions yield aldehyde groups, which are not present elsewhere on the protein. Since this region lies away from the epitope binding site, it minimizes interference with antigen binding. Additionally, it leaves the lysine residues of the antibody, a readily accessible conjugation site, available for subsequent conjugations. The A-chain of toxins such as Ricin can be covalently linked to an antibody using known coupling chemistry, for example, using the heterobifunctional cross-linker N-succinimidyl-3-(2-pyridyl-dithio-propionate) (SPDP), or by reductive amination. Cell culture studies with a cell toxin, the protein Ricin A (RTA) and a pH-sensitive polymer, PPAA, are described in the examples. When the RTA was added by itself to the cell culture, no cell death was noted, presumably due to the intracellular trafficking of the toxin to the lysosomes. When PPAA was physically mixed with the RTA, increasing concentrations of the mixture (at a fixed ratio of 3/1 PPAA/RTA) lead to increasing cell deaths. The polymer by itself was not toxic to cells. These observations indicate that the polymer is acting within the cell to enhance the action of the toxin, presumably by disrupting the endosomal membrane.

The examples further demonstrate the efficacy of an IgG conjugate and a biotinylated PEAA-streptavidin complex "conjugate" showing that the membrane disruptive polymers are still active when coupled to a protein. The examples also demonstrate that PPAA is as hemolytic when it is coupled to streptavidin as it is when it is free in solution.

Any of a variety of diagnostic agents can be employed. These can be administered alone or coupled to one or more therapeutic agents as described above. The agents can be radiolabelled, fluorescently labelled, enzymatically labelled and/or include dyes or magnetic compounds and other materials that can be detected using x-rays, ultrasound, magnetic resonance imaging ("MRI"), positron emission tomography (PET), computer assisted tomograph ("CAT"), single photon emission computerized tomography, fluoroscopy or other commonly used diagnostic technology. Examples of suitable materials for use as contrast agents in MRI include the gadolinium chelates currently available, such as diethylene triamine pentacetic acid (DTPA) and gadopentotate dimeglumine, as well as chelates of iron, magnesium, manganese, copper and chromium. Examples of materials useful for CAT and x-rays include iodine based materials, such as ionic monomers typified by diatrizoate and iothalamate, non-ionic monomers such as iopamidol, isohexyl, and ioversol, non-ionic dimers, such as iotrol and iodixanol, and ionic dimers, for example, ioxagalte. Useful ultrasound contrast agents that can be coupled to the membrane disruptive agent include an acoustic contrast agent that is preferentially bright when imaged with diagnostic ultrasound.

Radioactive compounds can also be used therapeutically. Radioisotopes include indium ("In"), iodine ("$^{131}$I"), and yttrium ("$^{90}$Y") isotopes, which can be cytotoxic.

These materials can be coupled to the conjugate using standard chemical techniques, or in some case, using recombinant technology, for example, to make a fusion protein. *J. Clin. Oncol.* 14, 1383-1400 (1996). Covalent linkages can be formed using chemical reactions well known to those of skill in the art. For example, glycoproteins often have saccharide moieties which can be oxidized to provide aldehyde groups. Aldehyde groups are known to react with amines to form Schiff bases, which can then be reduced with sodium cyanoborohydride in a process known as reductive amination. Peptides which have amine groups and carboxylic acid groups, polymers with carboxylic acid groups, and polymers and peptides with imidazole groups and other groups which hydrolyze phospholipid membranes at the pH range within the endosomes can be covalently coupled using methods well known to those of skill in the art. The agent can be coupled via a degradable linkage, such as an anhydride, ester, orthoester, amide, Schiff base or disulfide linkage.

Agents can be coupled ionically to a complex forming material, which is covalently coupled to the endosomal membrane disrupting agent. Oligonucleotides and other negatively charged materials such as anthracycline antitumor agents are known to form complexes with polycationic materials. Suitable polycationic materials include synthetic and natural polyamines, such as chitosan, poly(ethyleneimine) (PEI), poly(N,N-dimethylaminoethyl methacrylate) (PD-MAEMA), polyamidoamine (PAMAM), poly(vinyl pyridine), poly(imadazole), poly(vinyl amine) (obtained by hydrolysis of polyvinyl formamide), quaternized forms of these amines, and starburst dendrimers with cationic functional groups which are positively charged at lower pH. Polycationic materials can be covalently or ionically linked to the endosome disrupting agents and ionically complexed to negatively charged agents to be delivered. The complex may both stabilize and enhance endocytosis. Intercalating compounds can also be used for delivery of nucleic acids. For example, PEAA can be covalently linked to ethidium bromide. Other intercalating agents include some of the porphyrins and phthalocyanines.

Although described primarily with reference to transport into cells, the same technology can also be used to enhance transport out of cells or through cell layers. For example, one can enhance the transport of metabolites or other analytes in interstitial fluid or within the cytosol or across membrane barriers by administration of the disrupting agents and administration of an appropriate stimulus or stimuli such as light, ultrasound, electric field or change in temperature.

III. Endocytosis Enhancing Agents and Targeting Agents

Endocytosis enhancing agents can be ionically or covalently coupled, directly or indirectly, to the endosomal membrane disrupting agent. These can be used alone with the membrane disrupting agent or in combination with the membrane disrupting agent and an enhancer such as ultrasound, electric field, and/or stimuli. Exemplary endocytosis enhancing agents include antibodies, streptavidin-biotin, and membrane-receptor ligands such as the transferrin receptor peptides, which non-specifically bind the endosomal membrane disrupting agent to the cell where the agent is to be delivered; polycations; and phospholipases. Other ligands which interact with receptors on the cell surface include transferrin, galactose, asialoorosomucoid, insulin, cytokines such as interleukin 2, and growth factors such as epidermal growth factor, platelet derived growth factor, and nerve growth factor. Examples of conjugates of endosomal membrane disrupting agents and endocytosis enhancing agents include poly(ethylacrylic acid) (PEAA) directly conjugated to IgG and streptavidin conjugated to a ligand (e.g., IgG), then complexed with biotinylated PEAA (B-PEAA), to indirectly conjugate the endosomal membrane disrupting agent with the endocytosis enhancing agent.

Other compounds which appear to enhance endocytosis and/or membrane disruption may also be included in the formulation. Polycations, such as polylysine, are particularly effective when used in combination with negatively charged materials such as oligonucleotides. In another embodiment, the endosome membrane disrupting agent is ionically or covalently conjugated, directly or indirectly, with enzymes such as phospholipases, neuroamidases and sphingomylinases, which are capable of hydrolyzing lipids, thereby further enhancing membrane disruption. Suitable enzymes include the sphingomylinase isolated from the human placenta and phospholipase A2 from lysosomes. Other compounds which are not directly linked to the membrane disrupting agent or endocytosis enhancing agent but which are known to have these properties, such as glycerol, may also be included in the formulations.

Examples of molecules found on the surface of specific cell types include cell type specific antigens (which can be specific to species, individual, or tissue of origin), viral antigens (in the case of virally infected cells), and tumor antigens. These molecules can be targeted using antibodies, preferably monoclonal antibodies, most preferably human monoclonal antibodies or humanized antibodies, or using receptor-specific ligands. Tumor antigens are useful as targets for antibody-conjugated chemotherapeutic or cytotoxic agents. These are not specific markers for tumor cells in most cases; rather, they are overexpressed on tumor cells compared with normal tissue, or they are found in association with normal fetal tissue [CEA (Gold, et al., *J. Exp. Med.* 122, 467-481 (1965)), AFP (Abelev, *Adv. Cancer Res.* 14, 295-350 (1971)) or with normal progenitor cells of that organ in the adult (CEA). Tumor antigens can be localized in the tumor interstitium, on the tumor cell membrane, or in the tumor cell cytoplasm or nucleus.

Antigens that are found on cells in circulation and antigens expressed on tumor neovasculature are readily accessible to intravenous (i.v.) administered reagents. Antigens that are expressed on the surface of tissue or tumor cells are readily accessible to intralesional (i.l.) or intraperitoneal (i.p.) administered conjugates. Antigens secreted into the tumor interstitium are most accessible to i.l. administration.

The membrane disruption agents can be conjugated to cell ligands via spacer arms, such as polyethylene glycol (PEG). This could enhance the effectiveness of the endosomal membrane disruption agent. The effectiveness of disruption agents grafted to disruption polymer backbones (e.g., GALA-g-PAA) by conjugating or grafting them to the polymer via PEG spacer arms.

IV. Compounds which Minimize Lysosome Function

The formulations including membrane disruptive agents for disruption of endosomes can also include effective amounts of compounds which minimize lysosome function. Any compound which minimizes lysosome function without interfering with the efficacy of the agent to be delivered or the endosome disrupting agent can be used. Examples include lysosomal enzyme inhibitors in general. Other suitable compounds include amantadine, verapamil, chloroquine, chlorpromazine, monensin, and ammonium chloride.

V. Carriers

The compositions described herein can be incorporated into nano- and microparticles, including microspheres and microcapsules, liposomes, lipid vesicles, emulsions or polycationic complexes, using any method that does not destroy the activity of the agents to be delivered. In other embodiments, the disrupting agents are coupled by ionic, covalent or hydrophobic coupling of the polymers with cationic lipids or the particulate carriers. In one preferred embodiment, the endosomal disrupting agent is a polymer which is hydrophobic or has been hydrophobically modified for example by conjugation with cholesterol which can be incorporated into a liposome, especially cationic liposomes, so that the polymer is actually a part of the delivery system. These can be used alone with the membrane disrupting agent or in combination with the membrane disrupting agent and an enhancer such as ultrasound, electric field, and/or stimuli.

Microparticles and nanoparticles may be prepared using single and double emulsion solvent evaporation, spray drying, solvent extraction, solvent evaporation, phase separation, simple and complex coacervation, interfacial polymerization, and other methods well known to those of ordinary skill in the art. Methods developed for making microspheres for drug delivery are described in the literature, for example, as described in Doubrow, M., Ed, "Microcapsules and Nanoparticles in Medicine and Pharmacy," CRC Press, Boca Raton, 1992.

The compositions can also be administered in other physiologically acceptable vehicles, such as phosphate buffered saline, or other vehicles for topical, local, interstitial or intravenous administration.

B. Methods of Administration

The compositions can be administered to cells directly, topically, in suspension, as an ointment or spray, or to an animal, systemically, regionally (intralesionally) or locally. An effective dosage can be determined by an alteration in cell activity—for example, by measuring cell death, by detection of a diagnostic agent, or by measuring transport of a particular analyte. The compositions can be administered in a single bolus, continuously, or repeatedly.

In a preferred embodiment, the compositions are administered in vitro to the cells. For example, stem cells are removed from the body, treated with the compositions, alone or in combination with an enhancer such as ultrasound, in vitro to introduce genetic material into the cells, then reintroduced into the patient to be treated. In another example, bacterial cells are treated with the compositions and a stimulus is applied to cause membrane disruption. The stimulus can be a change in pH.

As described in the examples, a test which is predictive of disruption of endosomal membranes is the erythrocyte hemolysis test. The endosomal membrane disruptive properties is evaluated by determining the extent of lysis of erythrocytes. The hemolysis assay involves adding a small volume (e.g., 500 micrograms or 0.5 g of composition in a 1% solution, about 0.005 ml) solution of the composition to a red blood cell suspension of approximately $10^8$ cells (in about one ml), and incubating for one hour at 37° C. After incubation, the cells are centrifuged, and the absorbance of the supernatant is measured at 541 nm. This reflects the number of lysed cells.

If further studies are desired, one can label the compositions with a pH-dependent fluorophore as discussed in Geisow, M. J. Fluorescein Conjugates as Indicators of Subcellular pH. *Experimental Cell Research*, 150: 29-35 (1984). The endocytosis of the conjugates by cells, and their trafficking, is followed via visualization of the fluorophore. Depending on the emission maximum, one can determine whether the composition is in an environment of low pH (the endosome) or of physiological pH (the cytoplasm).

In those embodiments in which an endocytosis enhancing agent has been included in the compositions, these experiments can determine whether the agent's affinity has been altered by conjugation, as well as whether the membrane disruptive capabilities of the polymer are effective in stimulating endosomal release.

The compositions and methods described herein will be better understood with reference to the following non limiting examples.

EXAMPLE 1

Evaluation of the pH Sensitivity of PEAA-62K; PPAA

Objective:
The objectives of this work were to determine if random copolymers of acrylic acid-butyl acrylate and acrylic acid-propyl acrylate have potential to act as endosomal releasing agents. This can be determined by measuring the hemolytic activity of the above polymers at endosomal pH (5.5) and physiologic pH (7.4).

Protocol:
(I) Polymer Synthesis: Polymers and random copolymers of acrylic acid-propyl acrylate and acrylic acid-butyl acrylate were synthesized by free radical polymerization at various monomer feed ratios, in bulk, using AIBN as the initiator. The comonomer feed ratios are indicated in the relevant figures. The polymers were purified by ether precipitation.
(II) Hemolysis Assay: Fresh human blood was isolated in EDTA containing vacutainers, washed three times with 150 mM NaCl, and resuspended at a concentration of $10^8$ cells/ml in PBS buffer at either pH 5.5 or pH 7.4 or MES buffer, as noted. The polymers were dissolved in either DMSO or pH 10 buffered PBS. The appropriate volume of polymer solution was then added to the RBC solution and incubated for 1 hour at 37 degrees. The cells were then centrifuged and the degree of hemolysis was determined by measuring absorbance of the supernatant at 541 nM. A 100% lysis was determined by lysing the red blood cells in deionized water. The controls were RBCs suspended in buffer without polymer.

Poly(ethyl acrylic acid) with a label average molecular weight of 62,000 (PEAA-62K) (500 µg) was added to a red blood cell suspension of approximately $10^8$ cells in 100 mM MES at pH 5.1 or 100 mM sodium phosphate at pH 7.4, and incubated for one hour at 37° C. After incubation, the cells were centrifuged, and the absorbance of the supernatant was measured at 541 nm. The absorbance reflects the member of lysed cells. The control was approximately $10^8$ cells in the appropriate buffer.

PEAA achieved almost 100% erythrocyte lysis at pH 5.1 but less than 5% lysis at pH 7.4, as shown in FIG. 1A. Accordingly, the polymer is useful as an endosomal membrane disrupting agent.

PPAA (3 µg) was evaluated using the same experimental design. The red cells were suspended in 100 mM sodium phosphate at either pH 6.1 or 7.4.

Figure 1B:
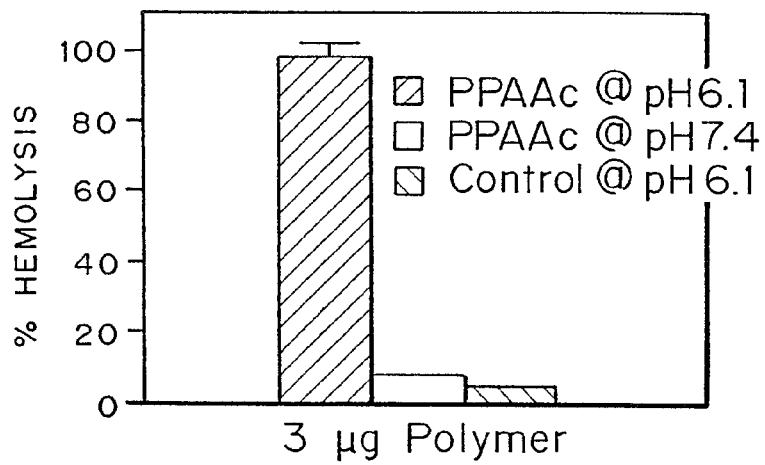
FIG. 1B is a graph showing the ability of poly(propyl acrylic acid) (PPAA) to lyse erythrocytes as a function of pH. Percent hemolysis is shown at a solution pH of 6.1 and 7.4, for 3 μg PPAA and for control.

As shown in FIG. 1B, PPAA achieved almost 100% erythrocyte lysis at pH 6.1 but less than 10% lysis at pH 7.4. Accordingly, the polymer is useful as an endosomal membrane disrupting agent.

The same experimental design was used as described, with the red cells in a buffer at pH 6.1, to compare PEAA and PPAA.

Figure 1C:
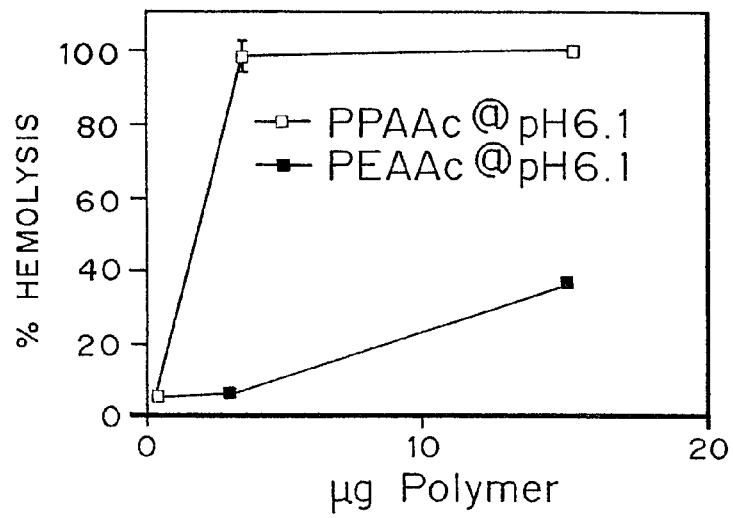
FIG. 1C is a graph comparing the ability of PPAA and PEAA to lyse erythrocytes as a function of pH. Percent hemolysis is shown at a solution pH of 6.1 for PPAA and PEAA.

As shown in FIG. 1C, significantly less PPAA than PEAA was needed to achieve substantial lysis at pH 6.1. Approximately 100% lysis was achieved with about 3 µg PPAA. Accordingly, PPAA is a significantly better endosomal membrane disrupting agent than PEAA.

The ability of PBAA to lyse erythrocytes was compared with that of PPAA at a pH of 6.1 and a pH of 7.4 using the same experimental design as described above.

Figure 1D:
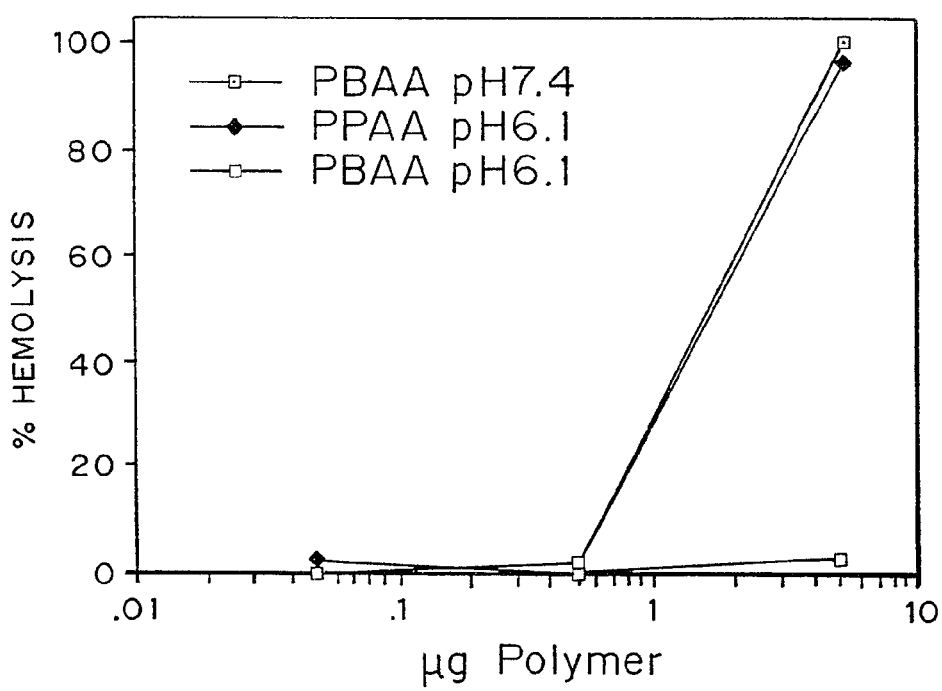
FIG. 1D is a graph comparing the ability of poly(butyl acrylic acid) (PBAA) and PPAA to lyse erythrocytes as a function of pH. Percent hemolysis is shown at a solution pH of 6.1 and 7.4 for PBAA and for 6.1 for PPAA.

The results are shown in FIG. 1D. PBAA showed less than 5% lysis at pH 7.4, up to a concentration of 5 µg. At pH 6.1, PBAA and PPAA demonstrated comparable lysis, yielding about 100% lysis at a concentration of about 5 µg. This data demonstrates that PBAA and PPAA have similar efficacy as endosomal membrane disrupting agents.

The ability of EA-AA (a random copolymer of ethyl acrylate and acrylic acid) to lyse erythrocytes was compared with that of PEAA at a pH of 5.5 using the same experimental design as described above.

Figure 1E:
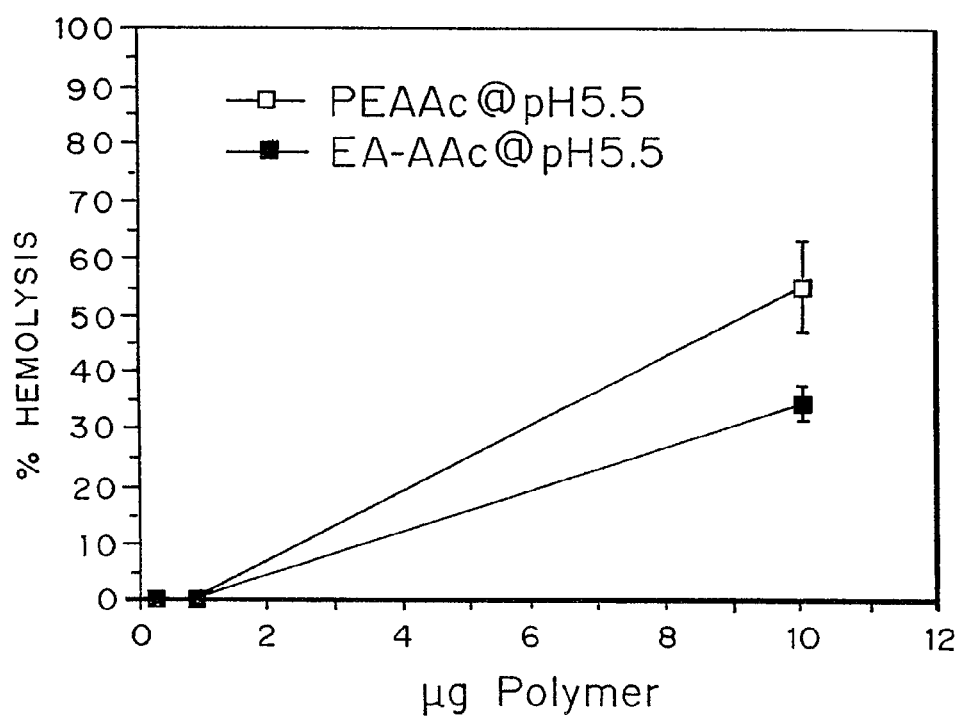
FIG. 1E is a graph comparing the ability of a random copolymer of ethyl acrylate and acrylic acid (EA-AA) and PEAA to lyse erythrocytes as a function of pH. Percent erythrocyte hemolysis is shown at a solution pH of 5.5.

The results are shown in FIG. 1E. The data demonstrate that the EA-AA copolymer was less effective than PEAA at pH 5.5 at hydrolyzing erythrocytes, achieving about 35% lysis at a concentration of 10 µg, compared to about 55% lysis for PEAA at a concentration of 10 µg.

Figure 1F:
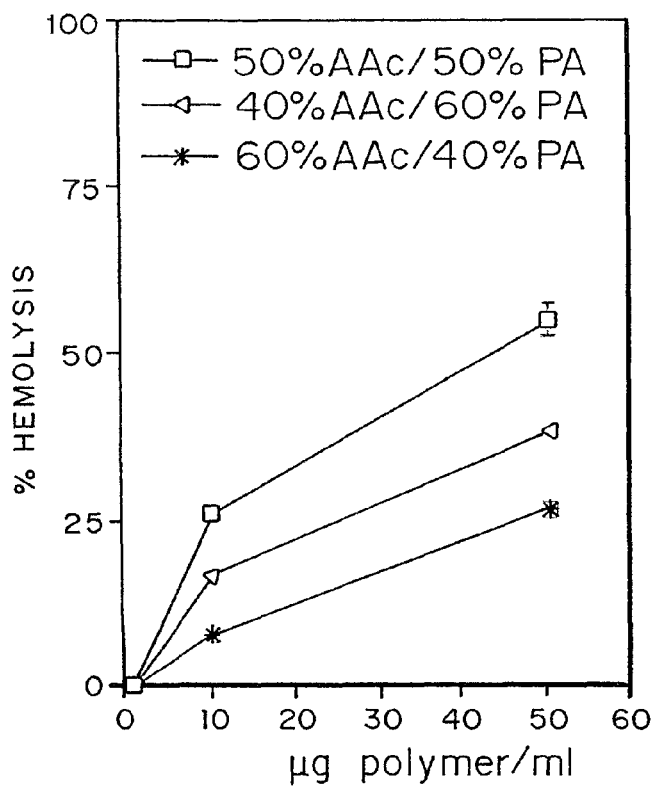
FIG. 1F is a graph comparing the effect of concentration of several random copolymers of acrylic acid and propyl acrylate on red blood cell hemolysis at pH 5.5.
Figure 1G:
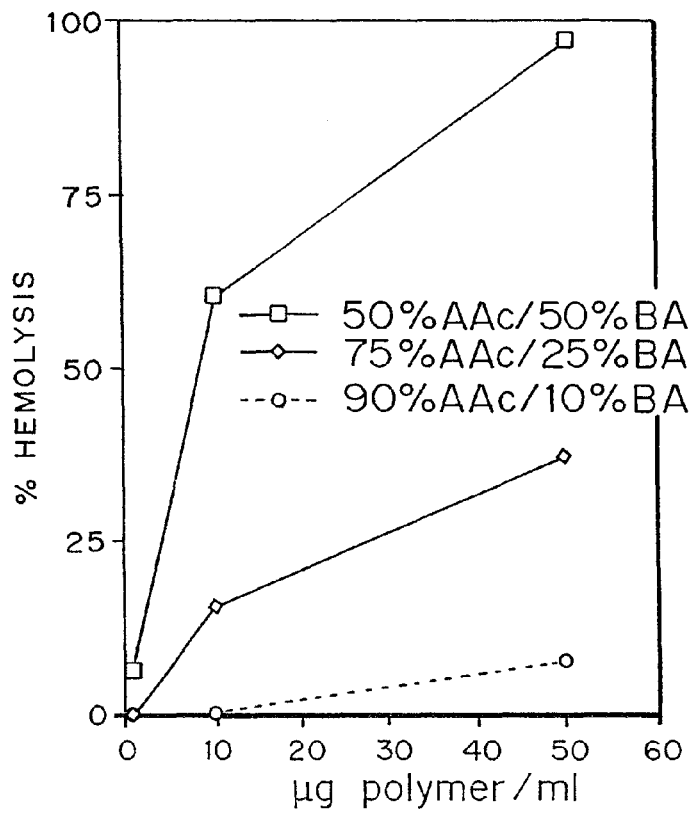
FIG. 1G is a graph comparing the effect of concentration of several random copolymers of acrylic acid and butyl acrylate on red blood cell hemolysis at Ph 5.5.

The concentration dependence of lysis was then determined. FIG. 1F shows the percent lysis of copolymers of AAc/PA: 50% AAc/50% PA, 40% AAc/60% PA; and 60% AAc/40% PA at pH 5.5. FIG. 1G shows the percent lysis of copolymers of AAc/BA: 50% AAc/50% BA; 75% AAc/25% BA; and 90% AAc/10% BA, at pH 5.5.

The results demonstrate that the random copolymers of propyl acrylate-acrylic acid are hemolytic at pH 5.5, the most hemolytic copolymer is the 50/50 copolymer, requiring 50 µg to cause 54% hemolysis of $10^8$ RBCs. The copolymers of propyl acrylate-acrylic acid show pH sensitive hemolysis, and the 50/50 copolymer causes only 30% hemolysis of $10^8$ RBCs at pH 7.4 as opposed to 54% at pH 5.5.

The copolymers of butyl acrylate-acrylic acid are extremely potent hemolytic agents. 10 μg of the 50/50 copolymer causes over 60% hemolysis of $10^8$ RBCs at pH 5.5. The butyl acrylate-acrylic acid copolymers are also pH sensitive. 10 μg of the 50/50 copolymer causes under 10% hemolysis of $10^8$ RBCs at pH 7.4

Both the random copolymers of acrylic acid-butyl acrylate and acrylic acid-propyl acrylate types of copolymers show pH sensitive hemolytic activity and are significantly more effective at inducing hemolysis at pH 5.5 then at pH 7.4. Furthermore, the hemolytic activity and the pH sensitivity of the above random copolymers can be rationally engineered by altering the comonomer composition.

EXAMPLE 2

Comparison of the pH Sensitivity of EALA with that of an EALA/Polyacrylic Acid Conjugate The ability of EALA to lyse erythrocytes was compared with that of an EALA/polyacrylic acid conjugate at a pH of 5.0 using approximately $10^7$ red blood cells in 100 mM dibasic $NaPO_4$, incubated at 37° C. for 20 minutes. A physical mixture of EALA and PAA was also tested.

Figure 2:
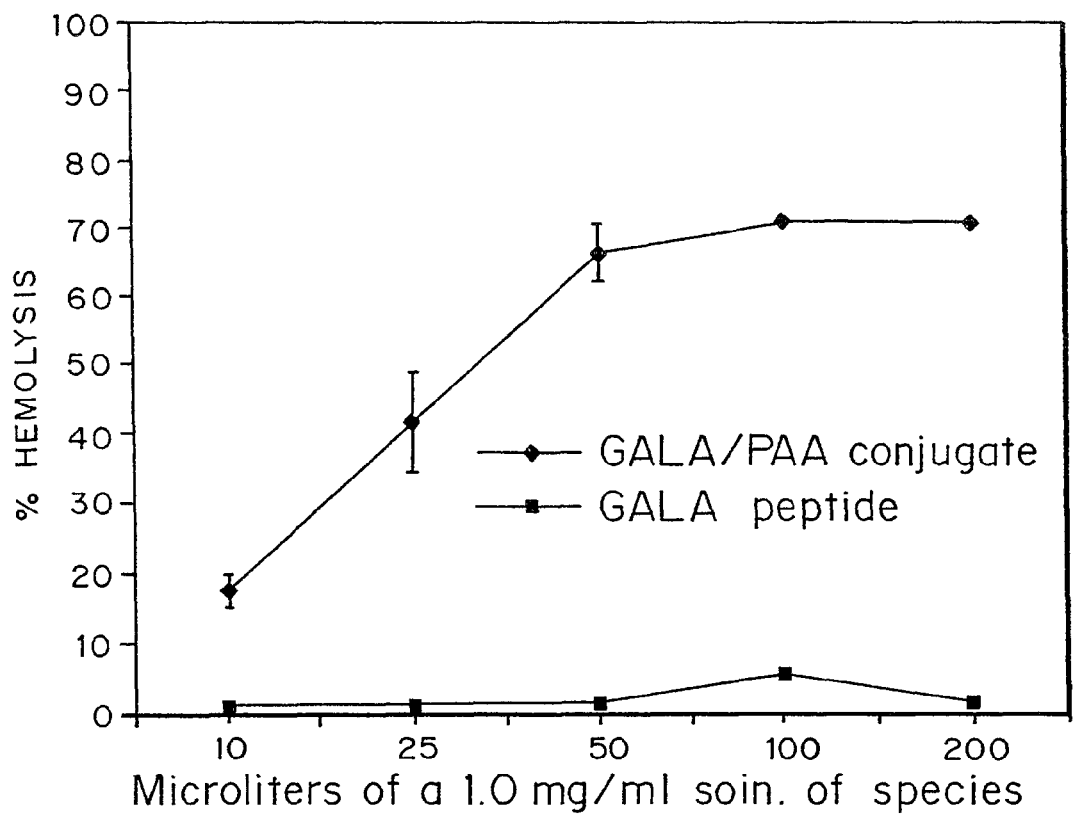
FIG. 2 is a graph comparing the ability of EALA (GALA) and an EALA/polyacrylic acid conjugate (GALA/PAA) to lyse erythrocytes. Percent erythrocyte hemolysis versus concentration is shown for both EALA and the EALA/poly-acrylic acid conjugate.

The results are shown in FIG. 2. The EALA peptide by itself, as well as the physical mixture of EALA with PAA, demonstrated a negligible amount of lysis whereas the conjugate yielded about 70% lysis at a concentration of about 100 μg.

EXAMPLE 7

Comparison of the pH Sensitivity of PEAA with that of an IgG/PEAA Conjugate and that of IgG alone The ability of PEAA, an IgG/PEAA conjugate, and IgG alone to lyse erythrocytes was compared by performing a hemolysis assay at a pH of 5.0 using approximately $10^8$ red blood cells in 100 mM dibasic sodium phosphate, and incubating at 37° C. for an hour. 1-ethyl-3-(3-dimethylaminopropyl)carbodiimide hydrochloride (EDC) was used to conjugate PEAA to rabbit immunoglobulin G (IgG). EDC reacts with the carboxyl groups to PEAA to form an amine-reactive intermediate, which then reacts with the lysine amine groups on IgG. The IgG was oxidized using 100 mM sodium periodate to yield reactive aldehyde groups on the carbohydrate moiety. Conjugation was realized via Schiff base formation between the end amine group of the amine-terminated PEAA and the aldehyde group on the IgG. This bond is reduced using 5 M sodium cyanoborohydride to yield a covalently bound conjugate of PEAA and IgG. The molar ratio of PEAA: IgG was 2:1.

Figure 3:
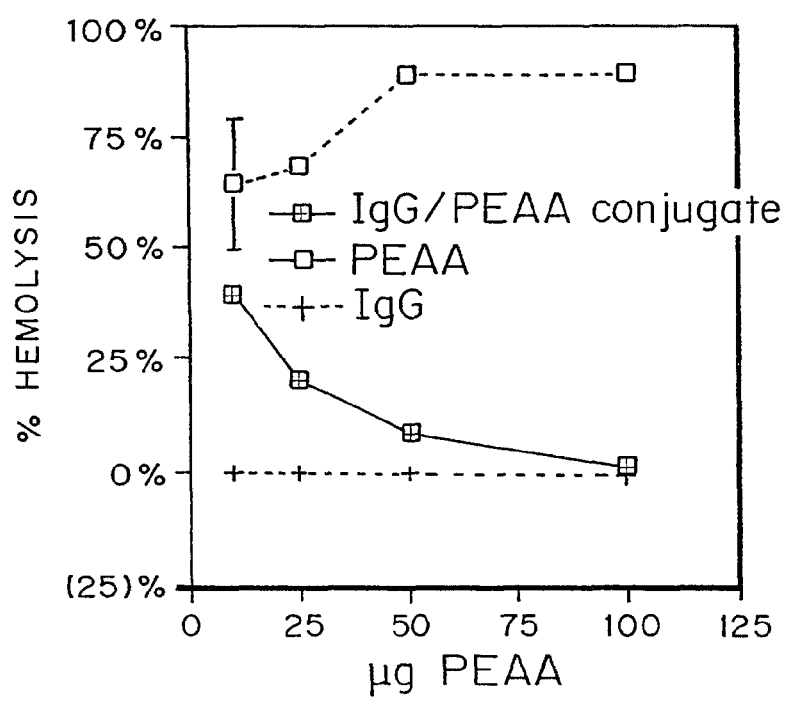
FIG. 3 is a graph comparing the ability of PEAA, an IgG/PEAA conjugate, and for IgG alone to lyse erythrocytes. Percent erythrocyte hemolysis versus concentration is shown for PEAA, an IgG/PEAA conjugate, and for IgG alone.

The ability of the IgG/PEAA conjugate to lyse erythrocytes was compared to that of free PEAA and that of free IgG. The results are shown in FIG. 3.

EXAMPLE 3

Comparison of the pH Sensitivity of Streptavidin/PEAA Conjugate with that of a B-PEAA Conjugate and that of a Streptavidin/B-PEAA Conjugate Objective:
To verify that complexation of PPAAc with a protein does not affect its ability to disrupt cell membranes.
Protocol:
Biotinylation of PPAAc: Complexation with streptavidin via streptavidin-biotin affinity (stoichiometric ratios of PPAAc:streptavidin of both 3:1 and 1:1).

Figure 4A:
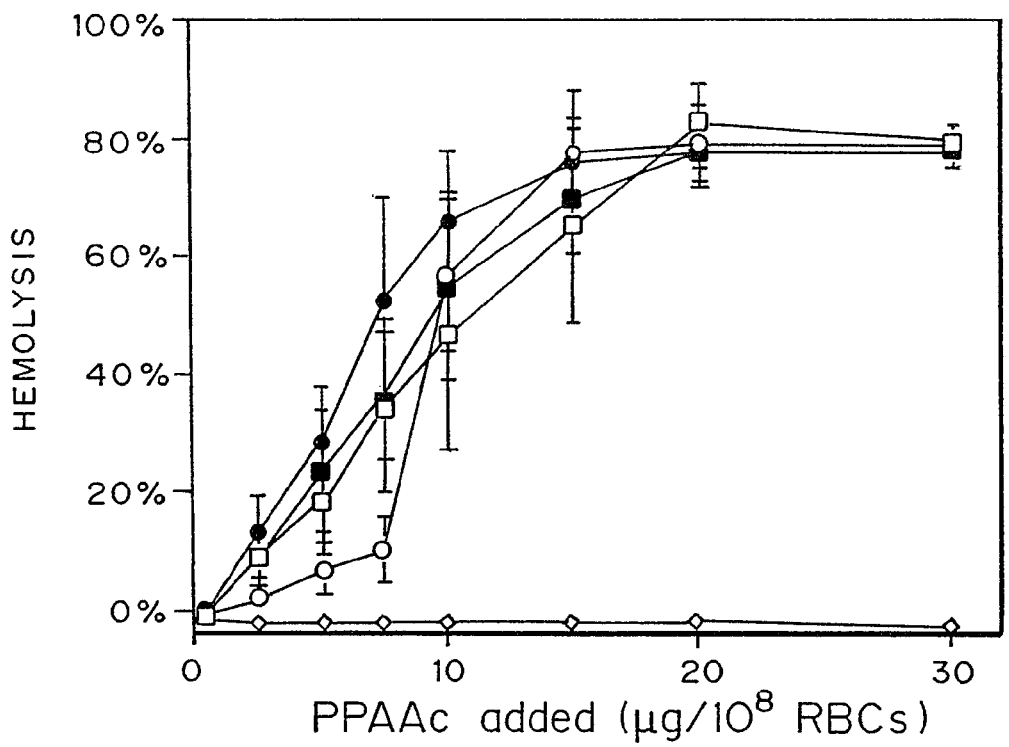
FIGS. 4A-D are graphs comparing the ability of PEAA, a streptavidin/PEAA conjugate, biotinylated-PEAA and a streptavidin/biotin-PEAA conjugate (at a ratio of either 3:1 or 1:1) to lyse erythrocytes. Percent erythrocyte hemolysis versus concentration of polymer is shown for PEAA, a streptavidin/PEAA conjugate, biotinylated-PEAA and a streptavidin/biotin-PEAA conjugate is shown in FIGS. 4A and 4B; percent erythrocyte hemolysis as a function of pH is shown in FIGS. 4C and 4D.
Figure 4B:
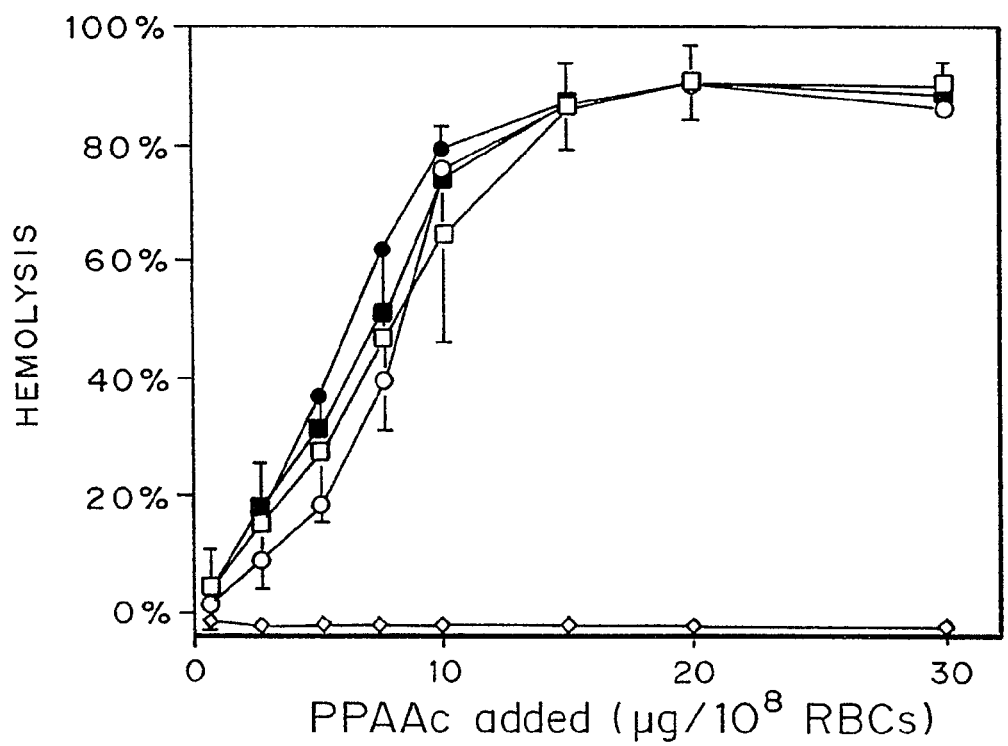
Figure 4C:
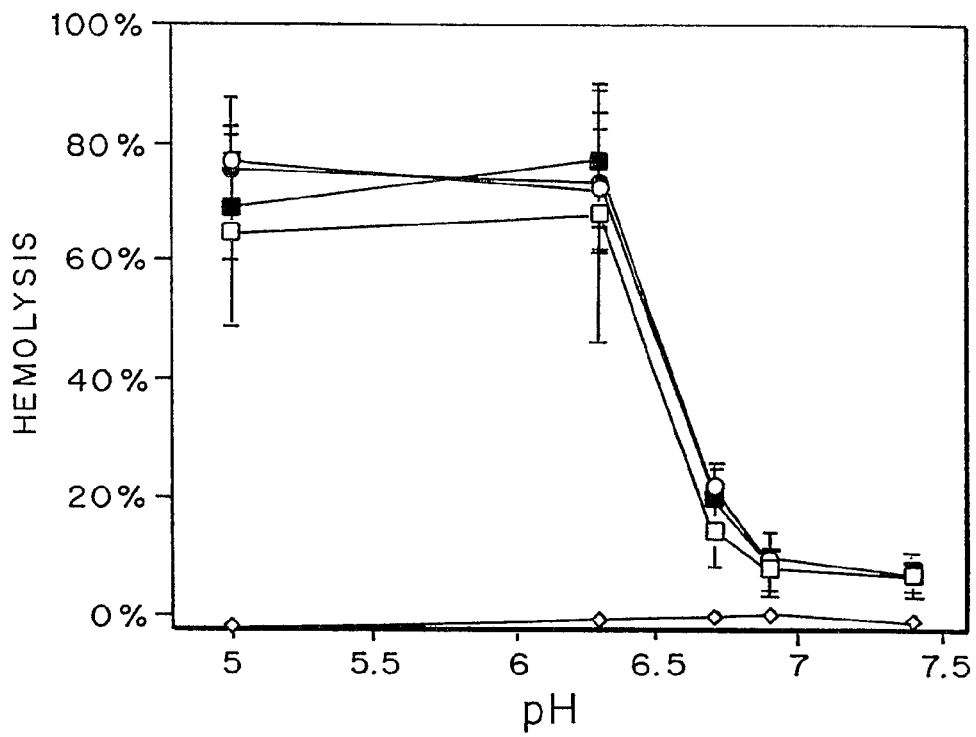
Figure 4D:
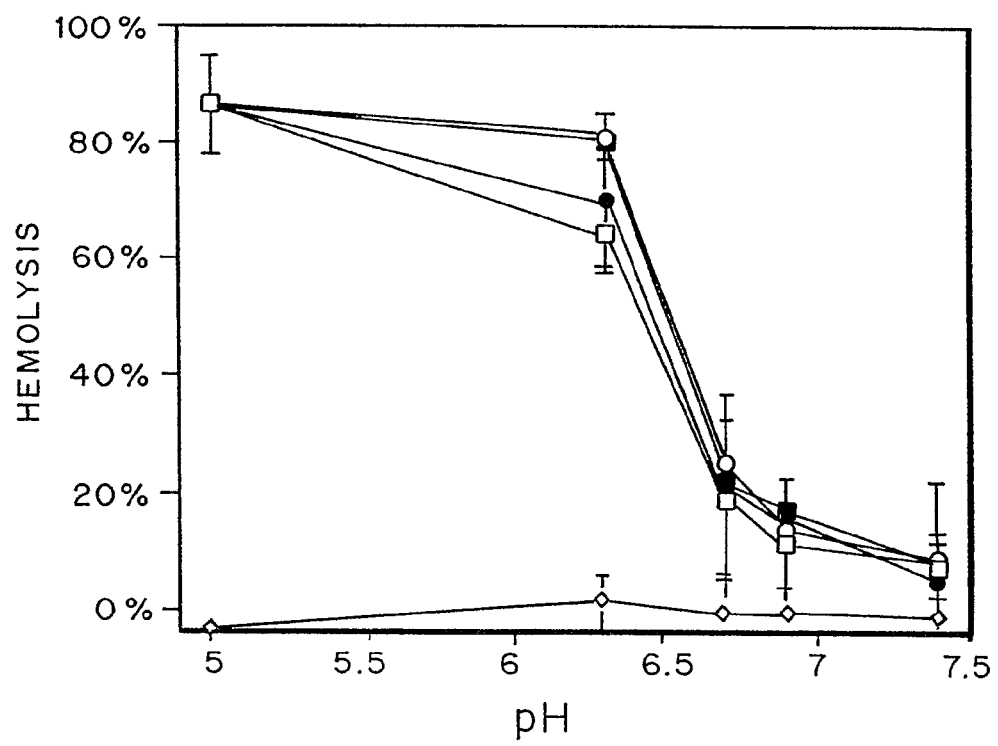

RBCs harvested by centrifuging whole blood for four minutes. Washed three times with 100 mM dibasic sodium phosphate at desired pH. Resuspended and diluted to $10^8$ RBCs per 200 μl. Each tube contained 800 μl of buffer, 200:1 of the RBC suspension, and the polymer sample. Each sample done in triplicate, and repeated to verify reproducibility. Tubes incubated for an hour and a half at 37° C. Tubes spun for five minutes at full speed in the microcentrifuge. Lysis determined by measuring the absorbance of the supernatant at 541 nm, reflecting the amount of hemoglobin released into the supernatant. Percent hemolysis calculated assuming 100% lysis by the red blood cells in water. Controls of RBCs in buffer with no polymer or in buffer with added streptavidin also run. The abilities of four different streptavidin and PEAA samples to lyse erythrocytes were compared by performing a hemolysis assay at a pH of 5.0 using approximately $10^8$ red blood cells in 100 mM dibasic sodium phosphate, and incubating at 37° C. for an hour. The four samples were biotinylated PEAA ("B-PEAA"), amine-terminated PEAA, a physical mixture of streptavidin and amine-terminated PEAA, and a complex of streptavidin and biotinylated PEAA. The complex formed in this last sample is a result of biotin-streptavidin affinity. In both samples containing protein and polymer, the molar ratio of PEAA:streptavidin was 3:1 (FIGS. 4A and 4C) or 1:1 (FIGS. 4B and 4D). This ratio was held constant for all concentrations of PEAA.

The results indicate that any modification of the PEAA (biotinylation or association with a protein) causes an increase in the hemolysis profile, in comparison to the plateau seen in the unmodified amine-terminated PEAA. No significant difference in percent hemolysis was observed as a function of pH (FIGS. 4C and 4D) or concentration between any of the different polymer-protein complexes. The percentage of hemolysis was pH and polymer concentration dependent.

EXAMPLE 4

Cell Death is Enhanced when PPAA is Mixed with a Toxin

Figure 5:
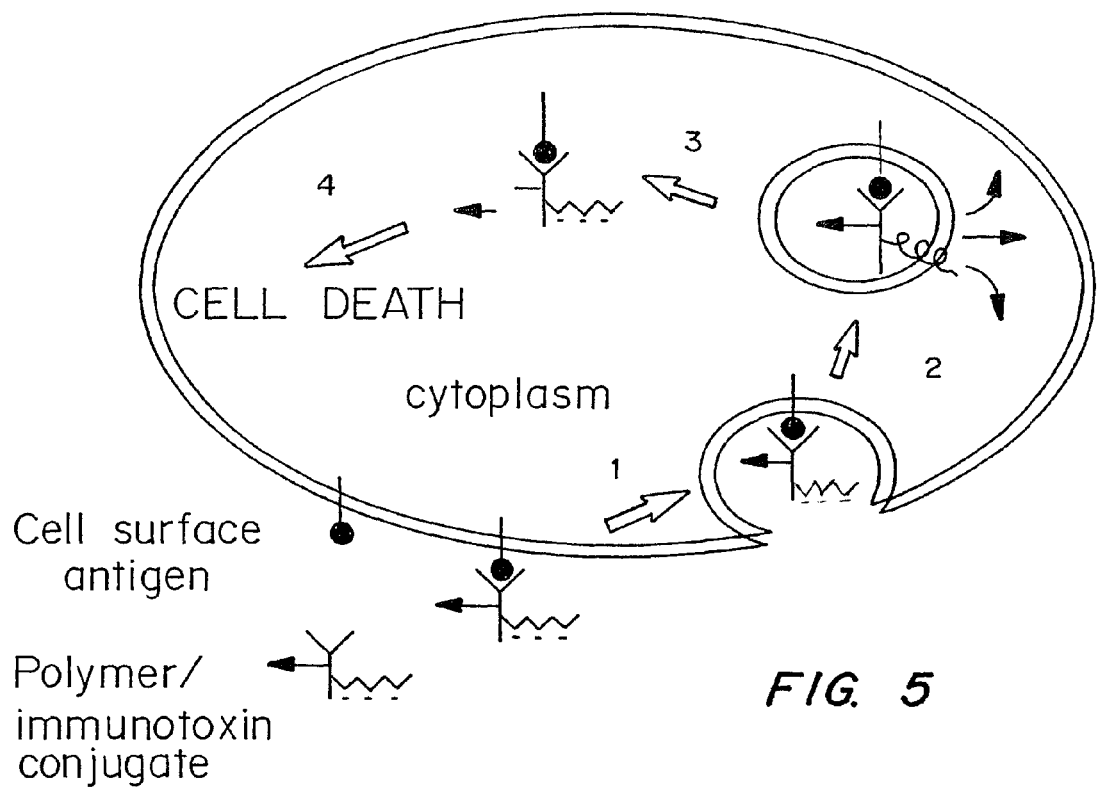
FIG. 5 is a schematic of immunotoxin therapy using pH-sensitive polymer-induced membrane disruption.

FIG. 5 is a schematic of immunotoxin therapy using pH-sensitive polymer-induced membrane disruption. Step 1 is receptor mediated endocytosis; step 2 is when the polymer-immunotoxin is taken up into the endosome; step 3 is when the endosomal pH of 5-6 triggers membrane lysis; and step 4 is when the immunotoxin is released into the cytoplasm, leading to cell death.

Objective:

Determine whether mixing PPAAc with ricin A chain (RTA) will enhance its endosomal release and toxicity. Endocytosis assay to quantify the inhibition of protein synthesis in cells treated with PPAAc and RTA, compared to cells treated with only PPAAc, only RTA, or untreated cells.

Protocol:

Ramos cells were suspended in leucine-free media at a concentration of 50,000 per well in 100 microliters. The cells were cultured 4 hrs at 37° C., then radiolabelled leucine (1 µCi of $^3$H-leucine per 25 µl media) was added, and the cells cultured for an additional 4 hrs at 37° C. 25 µl sample was removed to each well, with each sample in triplicate. Control wells contained 25 µl media. The wells were harvested onto filter paper and the amount of radioactivity counted using a scintillation counter. Polymer-toxin was added to treated cells at a ratio of PPAAc:RTA=3:1.

Figure 6:
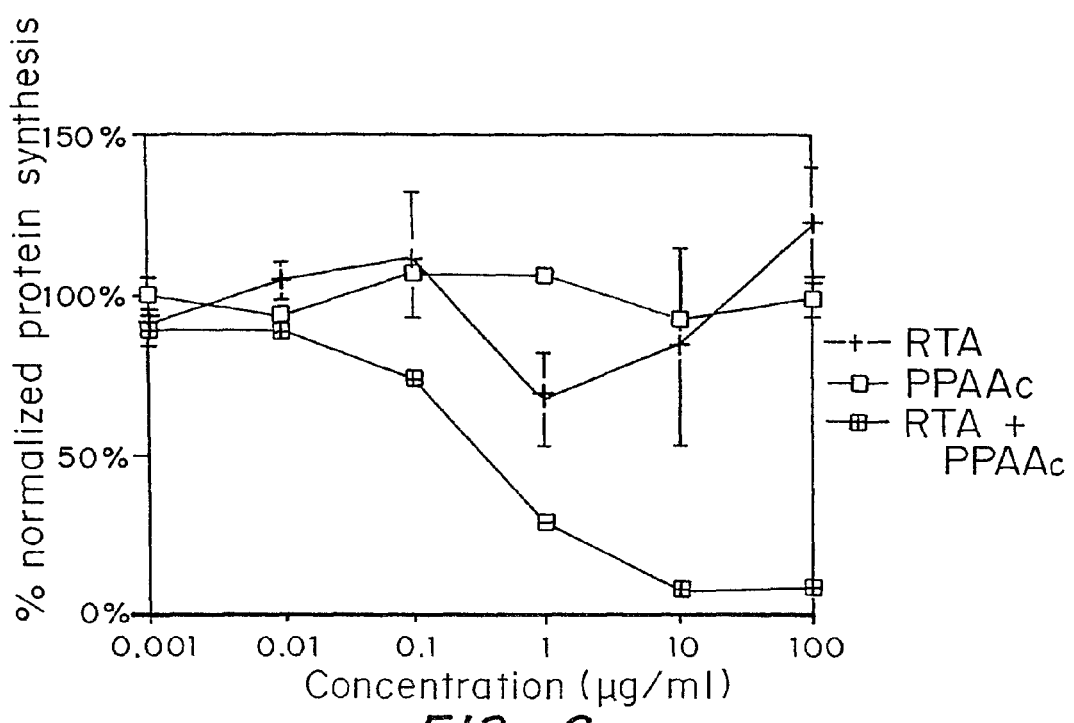
FIG. 6 is a graph of the enhancement of RTA toxicity by mixing with PPAAc, measured as percent normalized protein synthesis as a function of concentration of polymer (μg/ml) for RTA, PPAAc, and RTA+PPAAc.

Results:

As shown by FIG. 6, no cell death was observed when the RTA was added by itself to the cell culture, presumably due to the intracellular trafficking of the toxin to the lysosomes. When PPAA was physically mixed with the RTA, increasing concentrations of the mixture (at a fixed ratio of 3:1 PPAA: RTA) led to increasing numbers of cell deaths. The polymer by itself was not toxic to cells. These results demonstrate that a mixture of PPAAc and RTA causes inhibition of protein synthesis in a concentration dependent manner at concentrations where RTA alone is non-toxic. These observations indicate that the polymer is acting within the cell to enhance the action of the toxin, presumably by disrupting the endosomal membrane.

EXAMPLE 6

Hemolytic Activity of PEAA is Enhanced when Combined with Tone-Burst Ultrasound

In the past decade, localized drug treatment and gene therapy in vivo for disease and cancer has become a major area of research. One of the major obstacles for this technique is getting the drugs inside the cell once it has been delivered to the desired location inside the body. Cells have an effective defense against foreign bodies and organisms that attempt to invade its intracellular environment. Sonoporation has been looked upon as a possible solution to this problem. Electroporation and other techniques have been used in the past to increase the permeability of cell membranes, but they are limited to in vitro studies. Using focused ultrasound, the cell membrane can be made permeable to macromolecules in vivo in a manner similar to electroporation. This would allow for the drugs to enter the targeted cells without exposing the rest of the tissue. The ability of ultrasound and the synthetic polymer lysing agent poly(2-ethylacrylic acid) (PEAA) to disrupt cell membranes over time using human erythrocytes as a model system was investigated. PEAA has the ability to create pores and channels in the plasma membrane in mildly acidic conditions (Chung et al., 1996). However, this effect is directly proportional to the number of polymers that interact with the cell membrane. This present study tests the influence of ultrasound on the hemolysis effect of PEAA below active concentrations as a function of incubation time (experiment A), pH and order of exposure of erythrocytes by PEAA and ultrasound (experiment B).

Methods

Blood Sample:

Fresh human blood was obtained for each experiment. The cells were washed three times with 150 nM NaCl solution. The cells were then diluted with phosphate buffered saline solution to give a final concentration of $2\times10^8$ cells/m 1. The pH of this solution is 6.1, which is required for the activity of the PEAA, or 7.4, which inactivates PEAA, depending on the choice of experiment. In either case, a total of 1 mL of the cell suspension was pipetted into sample tubes constructed from polyester heat shrink tubing (Advanced Polymers, Inc., Salem N.H.) and placed at the focus of the power transducer.

Acoustic Setup:

All ultrasound treatments were conducted in a 16.5 cm×12.5 cm×12.5 cm acrylic tank containing degassed phosphate buffered saline (PBS). The temperature in the tank was maintained at 37° C. using a heating system. The tank is designed to keep the sample tube in the focus of the transducer at all times. A 70 mm diameter focused power transducer with a focal width of 15.mm and focal length of approximately 12 mm (Sonic Concepts, Woodinville, Wash.) is affixed to one wall of the tank. A radiation force balance was used to calibrate the power transducer. The single element 1.1 MHz transducer transmits a 10 ms tone burst (PRF=1 Hz) with a SATA intensity of 2200 W/cm2. A silicone absorber is placed at the opposite end of the tank to reduce reflections. A passive cavitation detection technique (Atchley et al. 1988) is used to monitor acoustic signals for bubble formation. A 5 MHz focused hydrophone is positioned 90° to the beam path of the focused transducer. The hydrophone is mounted in the wall of the tank confocally with the power transducer. All acoustic signals received by the hyrdophone are displayed on a LeCroy 9304AM oscilloscope. (It turned out in all of the studies that ann increase in cavitation events when ultrasound was applied in the presence of the polymer correlated well with the increase in hemolysis levels.) The tank is cleaned and filled with degassed phosphate buffered saline (pH=7.4) at 37° C. and sample tubes are placed at the focus of the power transducer.

Each sample of diluted red blood cells was exposed to 150, 10 ms pulses of 1.1 MHz ultrasound waveform with a 1% duty cycle at an intensity of 2200 W/cm$^2$. Low cell numbers reduced the cavitation threshold, enhancing the potential for cell/bubble interactions, and the low duty cycle reduced the thermal effects.

Objective A:

The activity of the PEAA alone is dependent upon the pH of the solution and the incubation time period. The polymer changes its conformation to an active state at a pH of 6.1 and is incubated with a cell suspension at 37° C. for an hour to achieve maximum cell lysis. 10 micrograms of PEAA was added to 1 ml of the cell suspension and incubated before ultrasound exposure. To test for ultrasound/polymer synergy the sample was treated at t=0, 20, 40 or 60 minutes after PEAA injection. After ultrasound treatment, one group of cells was immediately spun in a microcentrifuge (Eppendorf 5410, Westbury, N.Y.) at 14,000 rpm for 2 min. The supernatant is then removed and the hemoglobin content is measured with a spectrophotometer at 541 nm. The other group of cells was returned to the water bath to incubate for the rest of the hour, after which those cell suspensions were spun down, etc, as above. In both cases, the results are normalized against 100% hemolysis achieved by mixing the blood sample with distilled, deionized water.

Figure 7A:
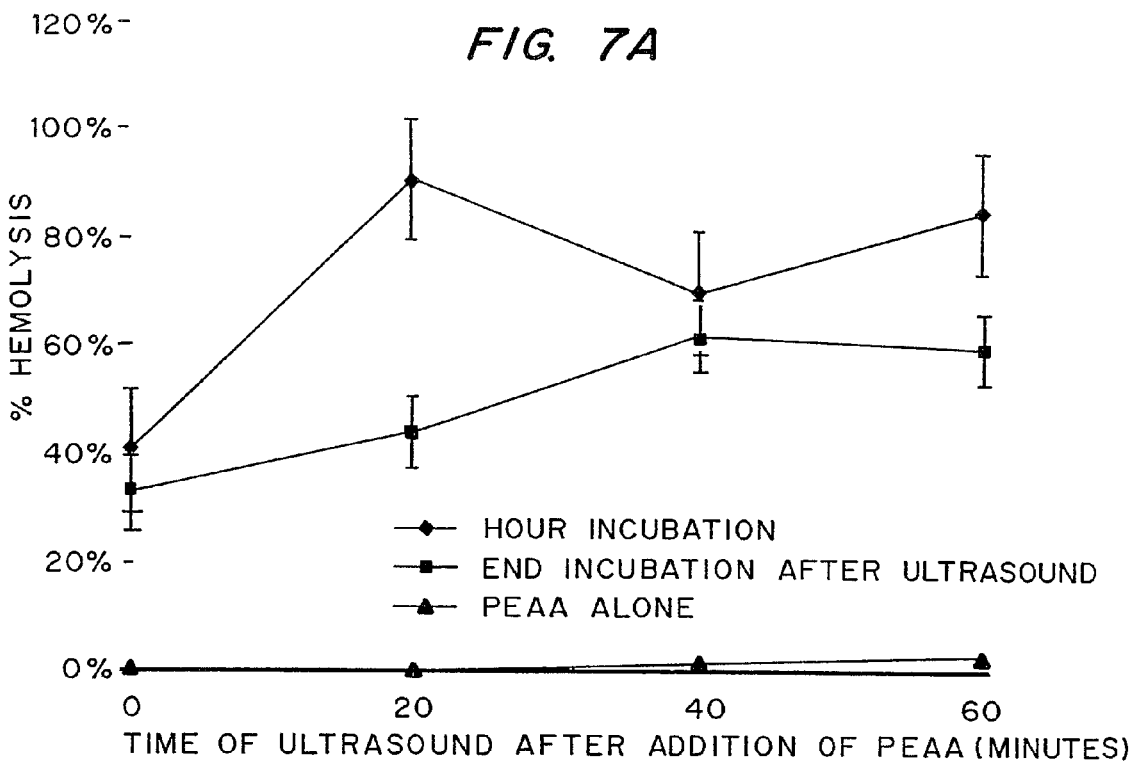
FIG. 7A is a graph of the effect of the combination of PEAA and ultrasound on hemolysis of erythrocytes (percent hemolysis over time in minutes).

Results A:

In preliminary tests on the effects of ultrasound and PEAA alone on human erythrocytes, it was determined that for 150 tone bursts, exposing the cells to less than 3000 W/cm$^2$ or less than 50 micrograms of PEAA produced insignificant hemolysis levels. FIG. 7A shows optimal levels of hemolysis when the polymer is allowed to incubate with the erythrocytes for at least 20 minutes before ultrasound treatment, and either returned back to the bath, or spun down immediately. There was little difference in the percent hemolysis in this first set of experiments (FIG. 7A).

Objective B:

The objective of this experiment was to test the effects of pH and order of exposure of erythrocytes to PEAA for one hour and ultrasound. For this experiment, the pH of the cell suspension was either 6.1 or 7.4. For the case of pH=6.1, in one experiment the ultrasound was applied before introducing the PEAA. In another experiment, the ultrasound was applied after the introduction of PEAA. For the case of pH=7.4, the ultrasound was applied after the introduction of PEAA.

Figure 7B:
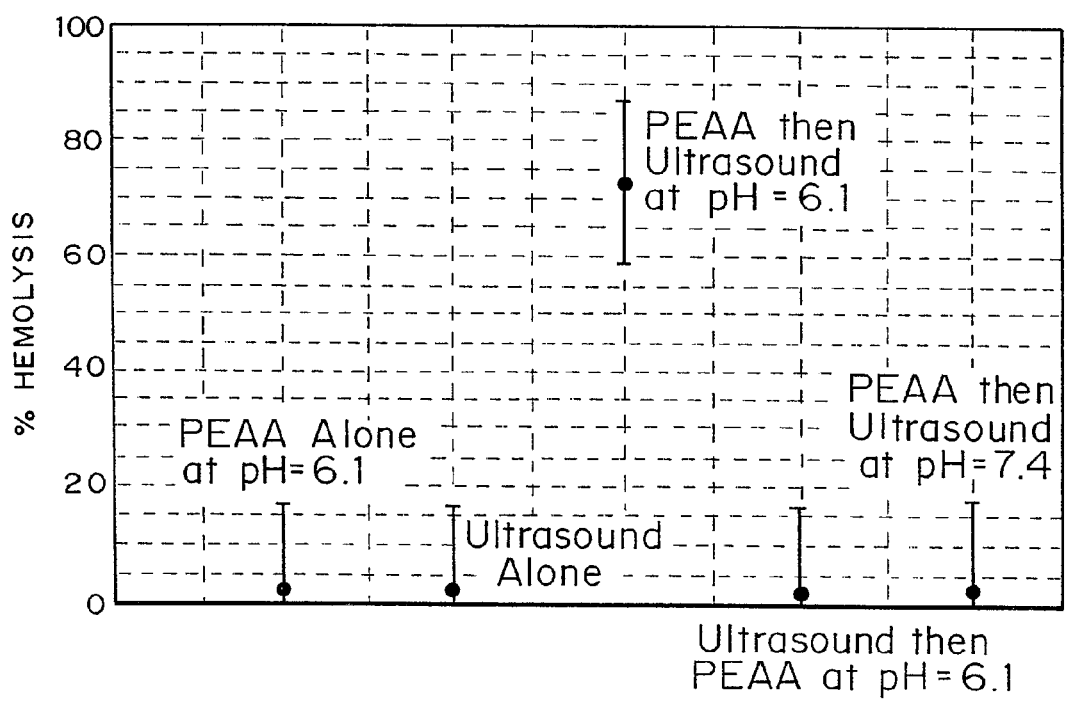
FIG. 7B is a graph of the percent hemolysis for PEAA, ultrasound, PEAA followed by ultrasound at pH 6.1, ultrasound followed by PEAA at pH 6.1, and PEAA followed by ultrasound at pH 7.4.

Results B:

The pH of the cell suspension and the presence of PEAA during ultrasound treatment were definitely important for the production of an enhancement of the effect of PEAA. The conformation of the polymer structure is dependent upon the pH of the solvent in which the PEAA is dissolved. Treating the cells at pH=7.4 or applying ultrasound before mixing the suspension with PEAA and incubating for an hour at pH=6.1 produced little to no hemolysis (FIG. 7B), while at a pH of 6.1, ultrasound applied to erythrocytes in the presence of PEAA produced profound levels of hemolysis. Thus, the presence of PEAA during ultrasound treatment is the key in this example.

The teachings of the references cited herein are specifically incorporated herein. Modifications and variations of the present invention will be obvious to those skilled in the art from the foregoing detailed description and are intended to be encompassed by the following claims.

The embodiments of the invention in which an exclusive property or privilege is claimed are defined as follows:

1. A composition for delivering a therapeutic or diagnostic agent to a cell, comprising (a) a transport agent and (b) a therapeutic or diagnostic agent, wherein the transport agent is effective in disrupting an endosomal membrane, wherein the therapeutic or diagnostic agent is covalently coupled to the transport agent, and wherein the transport agent is a poly(alkylacrylic acid) selected from the group consisting of poly(ethylacrylic acid), poly(propylacrylic acid), poly(butylacrylic acid), and mixtures thereof.

2. The composition of claim 1, wherein the transport agent is hydrophilic at pH from about 6.8 to about 7.5, and hydrophobic at pH from about 5.0 to about 6.5.

3. The composition of claim 1, wherein the transport agent is hydrophobic at pH from about 5.1 to about 5.5.

4. The composition of claim 1, wherein the therapeutic agent is selected from the group consisting of a nucleoside, a nucleotide, and an oligonucleotide.

5. The composition of claim 1, wherein the therapeutic agent is selected from the group consisting of a protein, lipoprotein, glycoprotein, and peptide.

6. The composition of claim 1, wherein the therapeutic agent is selected from the group consisting of a sugar and a polysaccharide.

7. The composition of claim 1, wherein the therapeutic agent is a toxin selected from the group consisting of ricin, diptheria toxin B chain, adenovirus peptide, influenza virus peptide, GALA peptide, abrin, modeccin, Pseudomonas exotoxin, bryodin, mistletoe lectin, Shiga toxin, Escherichia coli labile toxin, Pertussis toxin, cholera toxin, anthrax toxin, viscumin, spaorin, gelonin, momordin, trichlosanthin, and pokeweed antiviral protein.

8. The composition of claim 1, wherein the diagnostic agent is a radiolabeled agent.

9. The composition of claim 1, wherein the diagnostic agent is a fluorescently labeled agent.

10. The composition of claim 1, wherein the diagnostic agent is an enzymatically labeled agent.

11. The composition of claim 1, wherein the diagnostic agent is a contrast agent.

* * * * *